US009925355B2

United States Patent
Foley et al.

(10) Patent No.: US 9,925,355 B2
(45) Date of Patent: Mar. 27, 2018

(54) INTERMITTENT CATHETER ASSEMBLY AND KIT

(71) Applicant: Hollister Incorporated, Libertyville (IE)

(72) Inventors: Adam J. Foley, Ballina (IE); Jerome A. Henry, Castlebar (IE); David Hannon, Ballina (IE)

(73) Assignee: Hollister Incorporated, Libertyville, IL (US)

( * ) Notice: Subject to any disclaimer, the term of this patent is extended or adjusted under 35 U.S.C. 154(b) by 321 days.

(21) Appl. No.: 14/441,996

(22) PCT Filed: Mar. 14, 2013

(86) PCT No.: PCT/US2013/031230
§ 371 (c)(1),
(2) Date: May 11, 2015

(87) PCT Pub. No.: WO2014/074147
PCT Pub. Date: May 15, 2014

(65) Prior Publication Data
US 2015/0320970 A1 Nov. 12, 2015

Related U.S. Application Data

(60) Provisional application No. 61/725,311, filed on Nov. 12, 2012.

(51) Int. Cl.
*A61M 25/00* (2006.01)
*A61M 25/02* (2006.01)
(Continued)

(52) U.S. Cl.
CPC .... *A61M 25/0045* (2013.01); *A61M 25/0054* (2013.01); *A61M 25/0111* (2013.01);
(Continued)

(58) Field of Classification Search
CPC .... A61M 2025/006; A61M 2025/0098; A61M 2025/0293; A61M 2025/0681;
(Continued)

(56) References Cited

U.S. PATENT DOCUMENTS 3,084,693 A * 4/1963 Cathcart ............ A61M 25/0119
604/117
3,332,424 A * 7/1967 Minteer ............ A61M 25/0119
604/117

(Continued)

FOREIGN PATENT DOCUMENTS

| CN | 2240371 | 11/1996 |
|---|---|---|
| CN | 101300036 A | 11/2008 |

(Continued)

OTHER PUBLICATIONS

Canadian Office Action dated Apr. 22, 2016, for Application No. 2,891,118 entitled: Intermittent Catheter Assembly and Kit.

(Continued)

*Primary Examiner* — Adam Marcetich
(74) *Attorney, Agent, or Firm* — Cook Alex Ltd.

(57) ABSTRACT

An intermittent catheter assembly and kit comprising an elongated introducer element formed of a flexible material adapted for insertion into a urethra during a catheterization procedure. The introducer element has at least one slit extending longitudinally along a substantial portion of its length. The catheter assembly also includes an applicator having an opening, and a sheath having a first end that is secured to the applicator about the opening. The sheath also has a second end defining a discharge opening which is inverted relative to the first end of the sheath to define inner and outer sleeve portions. The inner sleeve portion defines a flow path for urine through the discharge opening. The applicator receives the introducer element through the opening and extends the outer sleeve portion over an outer (Continued)

surface of the elongated introducer element to separate it from the urethra.

30 Claims, 14 Drawing Sheets

(51) Int. Cl.
*A61M 25/01* (2006.01)
*A61M 25/06* (2006.01)

(52) U.S. Cl.
CPC ..... *A61M 25/0119* (2013.01); *A61M 25/0017* (2013.01); *A61M 25/0102* (2013.01); *A61M 2025/006* (2013.01); *A61M 2025/0098* (2013.01); *A61M 2025/0293* (2013.01); *A61M 2025/0681* (2013.01); *A61M 2202/0496* (2013.01); *A61M 2210/1096* (2013.01)

(58) Field of Classification Search
CPC .. A61M 2202/0496; A61M 2210/1096; A61M 25/0017; A61M 25/0045; A61M 25/0054; A61M 25/0102; A61M 25/0111; A61M 25/0119
See application file for complete search history.

(56) References Cited

U.S. PATENT DOCUMENTS

| | | | |
|---|---|---|---|
| 3,583,391 A * | 6/1971 | Cox | A61M 25/0119 600/585 |
| 3,621,848 A | 11/1971 | Magovern | |
| 3,702,610 A | 11/1972 | Sheppard et al. | |
| 3,861,396 A | 1/1975 | Vaillancourt et al. | |
| 3,894,540 A | 7/1975 | Bonner, Jr. | |
| 3,908,663 A * | 9/1975 | Viek | A61M 25/0119 600/581 |
| 4,062,363 A | 12/1977 | Bonner, Jr. | |
| 4,100,309 A | 7/1978 | Micklus et al. | |
| 4,227,533 A | 10/1980 | Godfrey | |
| 4,413,986 A | 11/1983 | Jacobs | |
| 4,465,481 A | 8/1984 | Blake | |
| 4,601,713 A * | 7/1986 | Fuqua | A61M 25/0023 604/103.14 |
| 4,610,671 A | 9/1986 | Luther | |
| 4,668,221 A | 5/1987 | Luther | |
| 4,762,738 A | 8/1988 | Keyes et al. | |
| 4,769,005 A | 9/1988 | Ginsburg et al. | |
| 4,772,279 A | 9/1988 | Brooks et al. | |
| 4,790,817 A | 12/1988 | Luther | |
| 4,790,831 A | 12/1988 | Skribiski | |
| 4,795,439 A | 1/1989 | Guest | |
| 4,840,622 A | 6/1989 | Hardy | |
| 4,883,699 A | 11/1989 | Aniuk et al. | |
| 4,906,238 A | 3/1990 | Greenfeld et al. | |
| 4,952,359 A | 8/1990 | Wells | |
| 4,954,129 A | 9/1990 | Giuliani et al. | |
| 4,994,047 A | 2/1991 | Walker et al. | |
| 5,002,526 A | 3/1991 | Herring | |
| 5,009,648 A | 4/1991 | Aronoff et al. | |
| 5,089,535 A | 2/1992 | Malwitz et al. | |
| 5,098,535 A | 3/1992 | Nakakoshi et al. | |
| 5,102,401 A | 4/1992 | Lambert et al. | |
| 5,195,962 A | 3/1993 | Martin et al. | |
| 5,270,086 A | 12/1993 | Hamlin | |
| 5,439,454 A | 8/1995 | Lo et al. | |
| 5,468,526 A | 11/1995 | Allen et al. | |
| 5,472,417 A | 12/1995 | Martin et al. | |
| 5,569,219 A | 10/1996 | Hakki et al. | |
| 5,601,538 A | 2/1997 | Deem | |
| 5,616,126 A | 4/1997 | Malekmehr et al. | |
| 5,676,688 A * | 10/1997 | Jaker | A61M 25/0017 604/104 |
| 5,688,459 A | 11/1997 | Mao et al. | |
| 5,776,611 A | 7/1998 | Elton et al. | |
| 5,792,114 A | 8/1998 | Fiore | |
| 5,800,412 A | 9/1998 | Zhang et al. | |
| 5,804,653 A | 9/1998 | Weng | |
| 5,904,703 A | 5/1999 | Gilson | |
| 5,985,394 A | 11/1999 | Mao et al. | |
| 6,017,334 A | 1/2000 | Rawls | |
| 6,030,369 A | 2/2000 | Engelson et al. | |
| 6,063,063 A | 5/2000 | Harboe et al. | |
| 6,066,120 A | 5/2000 | Whiteside | |
| 6,071,618 A | 6/2000 | Cook, Jr. et al. | |
| 6,090,075 A | 7/2000 | House | |
| 6,213,990 B1 | 4/2001 | Roempke | |
| 6,217,569 B1 | 4/2001 | Fiore | |
| 6,447,835 B1 | 9/2002 | Wang et al. | |
| 6,468,245 B2 | 10/2002 | Alexandersen | |
| 6,471,684 B2 | 10/2002 | Dulak et al. | |
| 6,488,659 B1 | 12/2002 | Rosenman | |
| 6,585,721 B2 | 7/2003 | Fiore | |
| 6,627,586 B1 | 9/2003 | Brooks et al. | |
| 6,656,146 B1 | 12/2003 | Clayman et al. | |
| 6,664,333 B2 | 12/2003 | Wang et al. | |
| 6,713,140 B2 | 3/2004 | McCormack et al. | |
| 6,726,654 B2 | 4/2004 | Rosenman | |
| 6,942,635 B2 | 9/2005 | Rosenblatt et al. | |
| 6,960,224 B2 | 11/2005 | Marino et al. | |
| 6,976,973 B1 | 12/2005 | Ruddell et al. | |
| 7,037,295 B2 | 5/2006 | Tiernan et al. | |
| 7,128,862 B2 | 10/2006 | Wang | |
| 7,156,824 B2 | 1/2007 | Rosenman | |
| 7,182,906 B2 | 2/2007 | Chen | |
| 7,402,620 B2 | 7/2008 | McGhee | |
| 7,553,923 B2 | 6/2009 | Williams | |
| 7,601,158 B2 | 10/2009 | Ouse | |
| 7,641,757 B2 | 1/2010 | Kampa et al. | |
| 7,662,146 B2 | 2/2010 | House | |
| 7,731,740 B2 | 6/2010 | LaFont et al. | |
| 7,789,873 B2 | 9/2010 | Kubalak et al. | |
| 7,815,628 B2 | 10/2010 | Devens, Jr. | |
| 7,820,284 B2 | 10/2010 | Terry | |
| 7,824,517 B2 | 11/2010 | Kampa et al. | |
| 7,833,280 B2 | 11/2010 | Stack et al. | |
| 7,947,031 B2 | 5/2011 | DiMatteo et al. | |
| 8,143,368 B2 | 3/2012 | Domb et al. | |
| 8,168,249 B2 | 5/2012 | Utas et al. | |
| 8,187,254 B2 | 5/2012 | Hissink | |
| 8,388,583 B2 | 3/2013 | Stout | |
| 8,388,585 B2 | 3/2013 | Tomes | |
| 8,469,928 B2 | 6/2013 | Stout | |
| 8,518,019 B2 | 8/2013 | Green | |
| 8,569,402 B2 | 10/2013 | Henderson et al. | |
| 2001/0007060 A1 * | 7/2001 | Fiore | A61M 25/0017 604/171 |
| 2001/0044595 A1 * | 11/2001 | Reydel | A61F 2/95 604/98.02 |
| 2002/0016574 A1 | 2/2002 | Wang et al. | |
| 2003/0165647 A1 | 9/2003 | Kaneko et al. | |
| 2003/0187368 A1 | 10/2003 | Sata et al. | |
| 2003/0228434 A1 | 12/2003 | Bailey et al. | |
| 2004/0122382 A1 | 6/2004 | Johnson et al. | |
| 2004/0210180 A1 | 10/2004 | Altman | |
| 2004/0220550 A1 | 11/2004 | Schryver | |
| 2004/0230177 A1 | 11/2004 | DiMatteo et al. | |
| 2004/0232589 A1 | 11/2004 | Kawabata et al. | |
| 2005/0049577 A1 | 3/2005 | Snell et al. | |
| 2005/0109648 A1 | 5/2005 | Kerzman et al. | |
| 2005/0131386 A1 | 6/2005 | Freeman et al. | |
| 2005/0163844 A1 | 7/2005 | Ashton | |
| 2005/0197627 A1 | 9/2005 | Huang et al. | |
| 2005/0218154 A1 | 10/2005 | Selsby | |
| 2005/0277862 A1 | 12/2005 | Anand | |
| 2005/0283111 A1 | 12/2005 | Maurice | |
| 2006/0020164 A1 * | 1/2006 | Butler | A61B 1/00151 600/115 |
| 2006/0122566 A1 * | 6/2006 | Huang | A61M 25/0119 604/271 |
| 2006/0173422 A1 | 8/2006 | Reydel et al. | |
| 2006/0240064 A9 | 10/2006 | Hunter | |
| 2007/0043333 A1 | 2/2007 | Kampa et al. | |

(56) References Cited

U.S. PATENT DOCUMENTS

| | | |
|---|---|---|
| 2007/0078412 A1 | 4/2007 | McGuckin, Jr. et al. |
| 2007/0088330 A1 | 4/2007 | House |
| 2007/0203502 A1 | 8/2007 | Makker et al. |
| 2007/0225649 A1 | 9/2007 | House |
| 2008/0015527 A1 | 1/2008 | House |
| 2008/0091145 A1 | 4/2008 | House |
| 2008/0097411 A1 | 4/2008 | House |
| 2008/0118544 A1 | 5/2008 | Wang |
| 2008/0147049 A1 | 6/2008 | House et al. |
| 2008/0171991 A1* | 7/2008 | Kourakis ........... A61M 25/0119 604/175 |
| 2008/0171998 A1 | 7/2008 | House |
| 2008/0172042 A1 | 7/2008 | House |
| 2008/0183262 A1 | 7/2008 | Dowling |
| 2008/0242940 A1* | 10/2008 | Stefanchik ....... A61B 17/22031 600/235 |
| 2008/0255510 A1 | 10/2008 | Wang |
| 2008/0268193 A1 | 10/2008 | Cherry et al. |
| 2008/0292776 A1 | 11/2008 | Dias et al. |
| 2008/0312550 A1 | 12/2008 | Nishtala |
| 2009/0018530 A1 | 1/2009 | Nielsen et al. |
| 2009/0036874 A1 | 2/2009 | Horowitz et al. |
| 2009/0250370 A1 | 10/2009 | Whitchurch |
| 2009/0264869 A1 | 10/2009 | Schmid et al. |
| 2010/0030197 A1 | 2/2010 | House |
| 2010/0049146 A1 | 2/2010 | Nielsen et al. |
| 2010/0098746 A1 | 4/2010 | King |
| 2010/0100116 A1 | 4/2010 | Brister et al. |
| 2010/0137743 A1 | 6/2010 | Nishtala et al. |
| 2010/0145315 A1 | 6/2010 | House |
| 2010/0198195 A1 | 8/2010 | Nishtala et al. |
| 2010/0204682 A1 | 8/2010 | Tanghoj et al. |
| 2010/0209472 A1 | 8/2010 | Wang |
| 2010/0215708 A1 | 8/2010 | Zumbuehl et al. |
| 2010/0297458 A1* | 11/2010 | Khemani ................. C08L 3/02 428/480 |
| 2010/0312255 A1 | 12/2010 | Satake et al. |
| 2010/0323189 A1 | 12/2010 | Illsley et al. |
| 2010/0324540 A1* | 12/2010 | Paulen .............. A61M 25/0017 604/544 |
| 2011/0034987 A1* | 2/2011 | Kennedy ................. A61F 2/95 623/1.11 |
| 2011/0049146 A1 | 3/2011 | Illsley et al. |
| 2011/0071507 A1 | 3/2011 | Svensson et al. |
| 2011/0114520 A1 | 5/2011 | Matthison-Hansen |
| 2011/0125135 A1 | 5/2011 | Ahmed |
| 2011/0160662 A1 | 6/2011 | Stout |
| 2011/0178425 A1 | 7/2011 | Nishtala |
| 2011/0190736 A1* | 8/2011 | Young ............... A61M 25/0017 604/544 |
| 2011/0212157 A1 | 9/2011 | Edelson et al. |
| 2011/0238163 A1 | 9/2011 | Andrews et al. |
| 2011/0268938 A1 | 11/2011 | Schuhmann |
| 2012/0035530 A1 | 2/2012 | Wang |
| 2012/0121919 A1 | 5/2012 | Nielsen |
| 2013/0131646 A1 | 5/2013 | Gilman |
| 2013/0345681 A1 | 12/2013 | Hong |

FOREIGN PATENT DOCUMENTS

| | | |
|---|---|---|
| DE | 10 2011 119160 A1 | 5/2013 |
| EP | 0010171 A1 | 4/1980 |
| EP | 0166998 B1 | 1/1986 |
| EP | 0613672 A1 | 9/1994 |
| EP | 0628586 B1 | 12/1994 |
| EP | 0692276 A2 | 1/1996 |
| EP | 1062920 A1 | 12/2000 |
| EP | 1110561 A2 | 6/2001 |
| EP | 1415671 | 5/2004 |
| EP | 2026846 A1 | 2/2009 |
| EP | 2301595 A1 | 3/2011 |
| EP | 2609956 A1 | 7/2013 |
| GB | 2083762 | 3/1982 |
| GB | 2496901 A | 5/2013 |
| JP | S-61209655 A | 9/1986 |
| JP | 01-136662 | 9/1989 |
| JP | 11151293 | 6/1999 |
| KR | 2000/065291 A | 11/2000 |
| KR | 100754057 B | 8/2007 |
| WO | WO 89/05671 A | 6/1989 |
| WO | WO 96/41653 A1 | 12/1996 |
| WO | WO 1998/058989 A1 | 12/1998 |
| WO | WO 2001/30696 | 5/2001 |
| WO | WO 2006/055847 A2 | 5/2006 |
| WO | WO 2006/071813 A2 | 7/2006 |
| WO | WO 2007/122269 A1 | 11/2007 |
| WO | WO 2007/140320 | 12/2007 |
| WO | WO 2010/043565 A1 | 4/2010 |
| WO | WO 2011/076211 A1 | 6/2011 |
| WO | WO 2012/163413 A1 | 12/2012 |
| WO | WO 2012/166967 A1 | 12/2012 |
| WO | WO 2014/193402 A1 | 12/2014 |

OTHER PUBLICATIONS

Notification of Transmittal of the International Search Report and the Written Opinion of the ISA for PCT/US2013/031230 dated Jul. 9, 2013 (Jul. 9, 2013).

Rachna N. Dave, Hiren M. Joshi, and Vayalam P. Benugopalan, Novel Biocatalytic Polymer-Based Antimicrobial Coatings as Potential Ureteral Biomaterial, Feb. 1, 2011, 44(2): 845-853.

Beom Soo Kim, Jeffrey S. Hrkach, Robert Langer, Biodegradable photo-crosslinked poly(ether-ester) networks for lubricious coatings, Biomaterials, vol. 21, Issue 3, Feb. 2000, pp. 259-265.

A.K. Singla, M. Chawla, Chitosan some pharmaceutical and biological aspects, an update, Journal of Pharmacy and Pharmacology, Aug. 2001, 53: 1047-1067.

FreeStyle Vie Flushable Colostomy Bag by CliniMed Ltd., retrieved from http://www.clinimed.co.uk/Stoma-Care/Products/Closed-Stoma-Bags/Freestyle-Vie-Flushable/Product-Design.aspx Jan. 1, 2014.

* cited by examiner

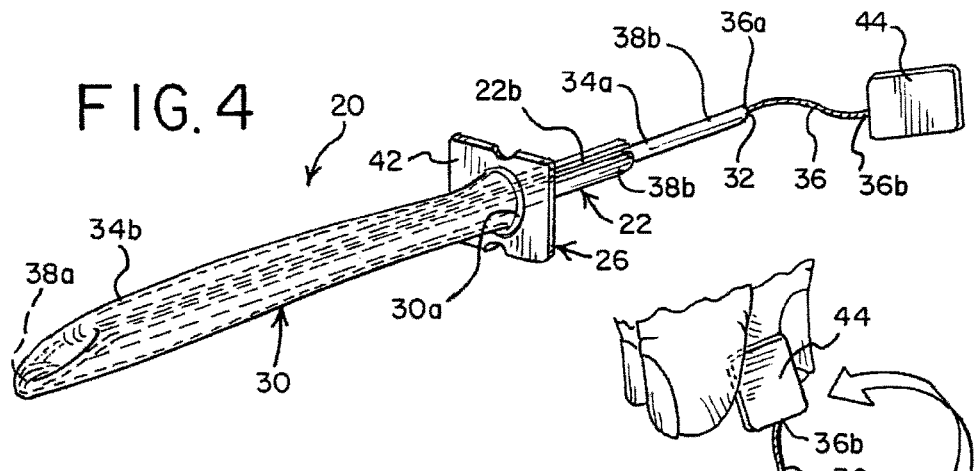
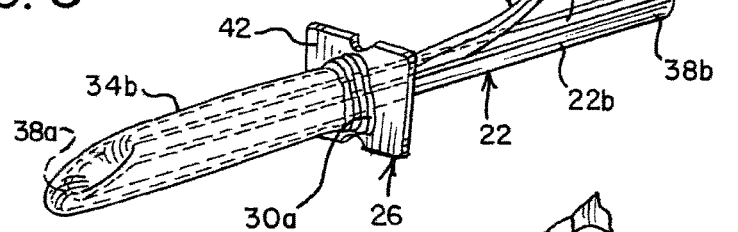
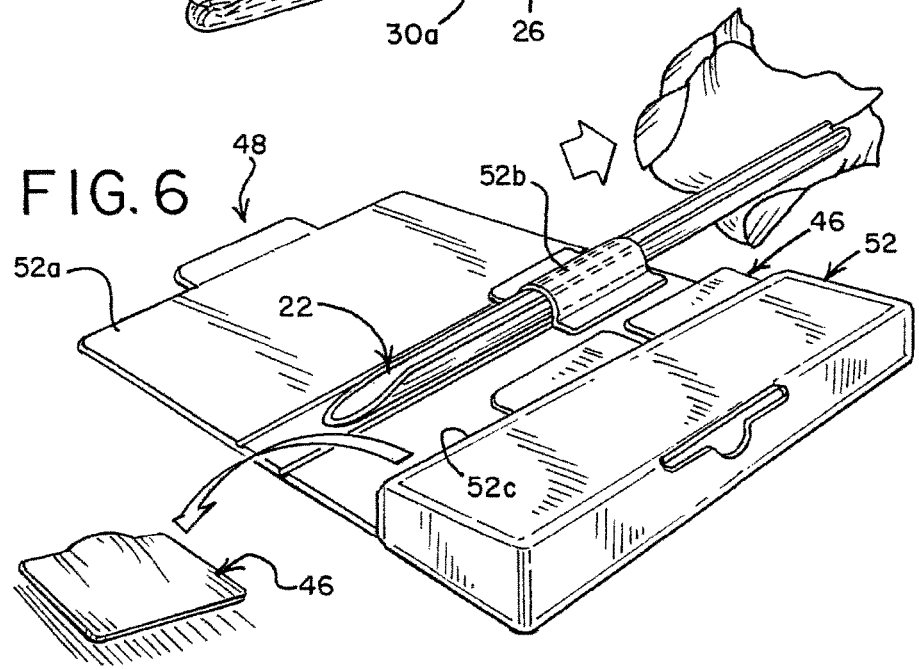

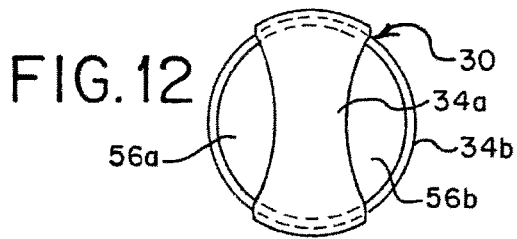
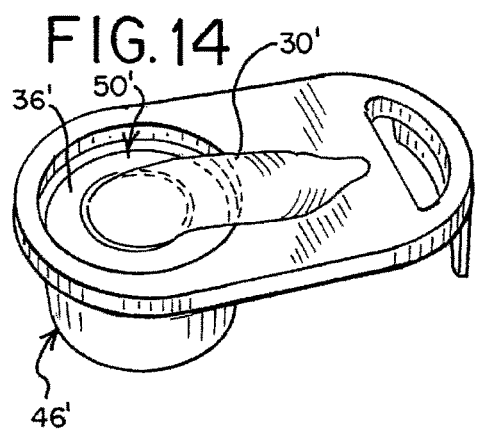
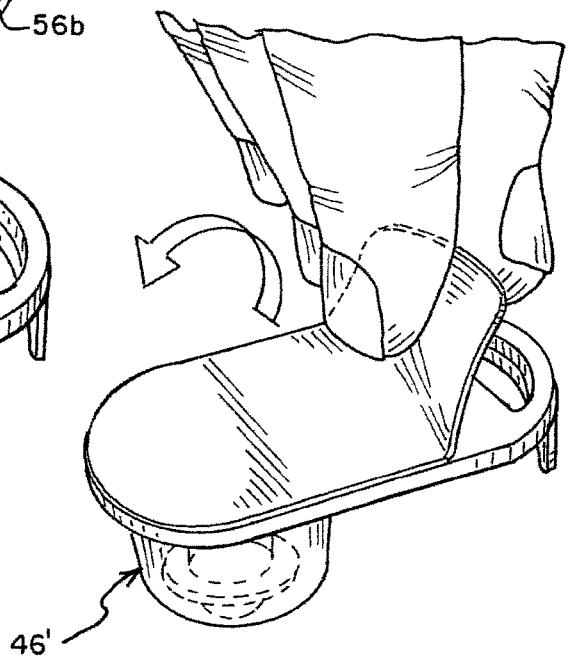
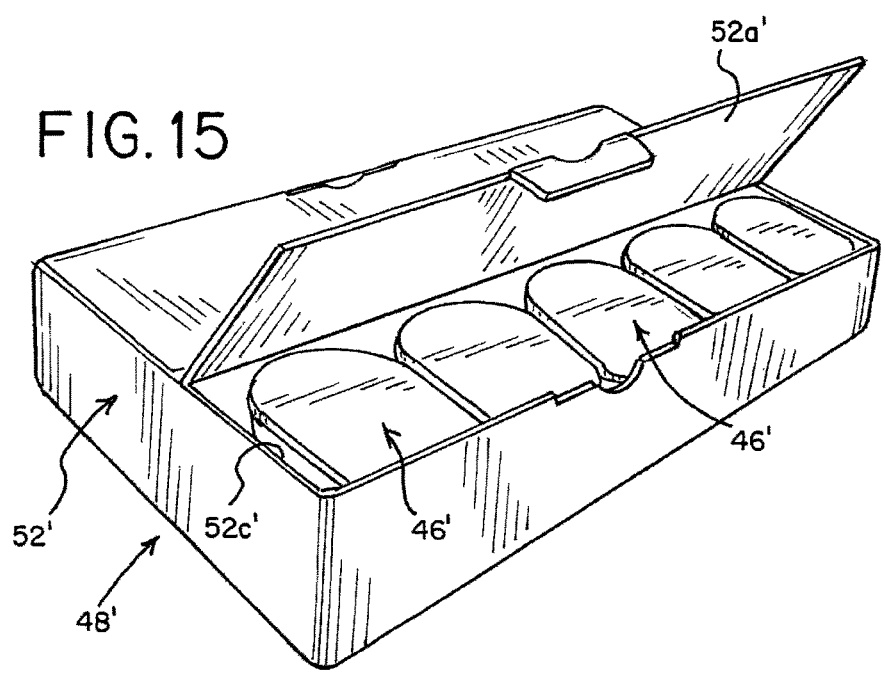

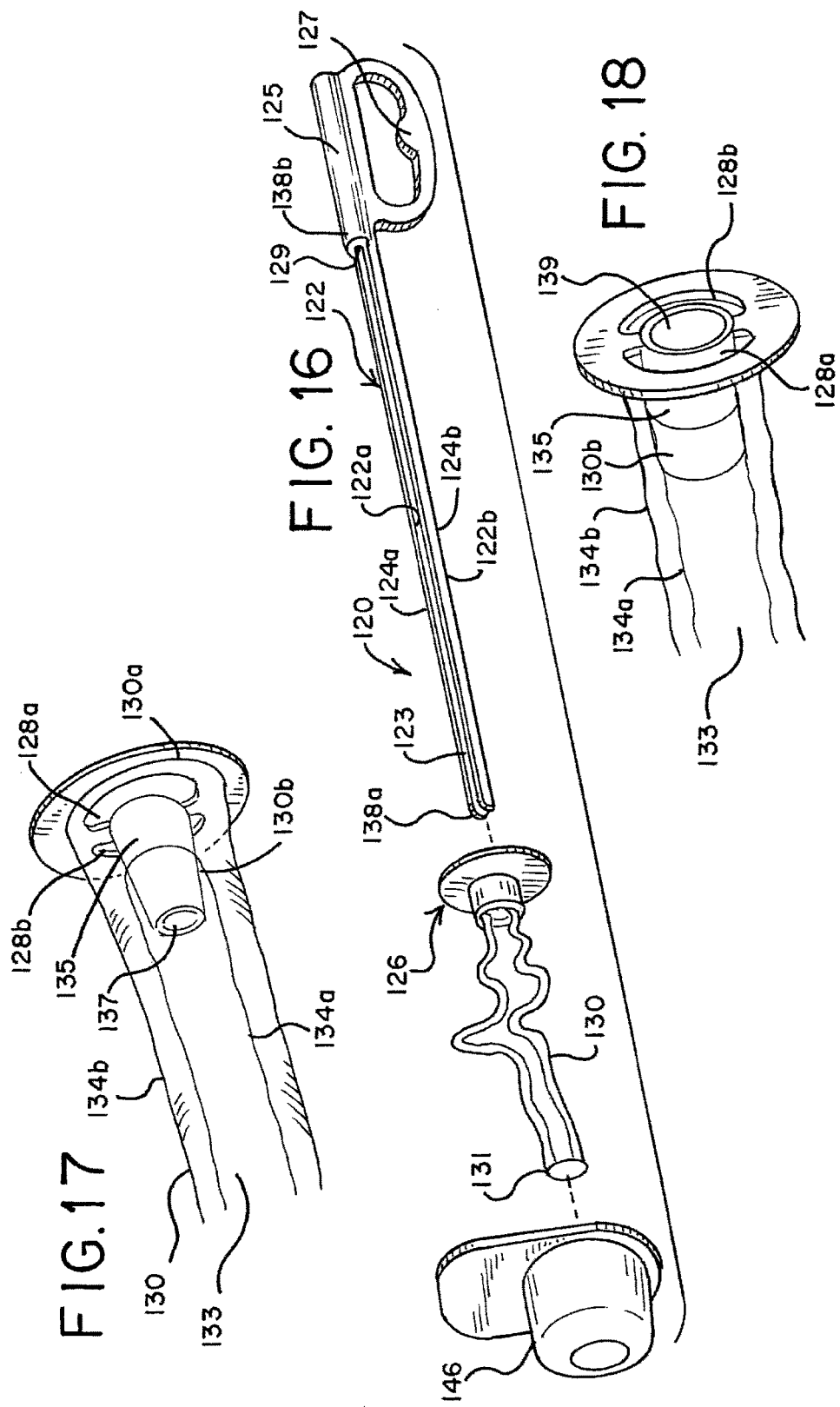

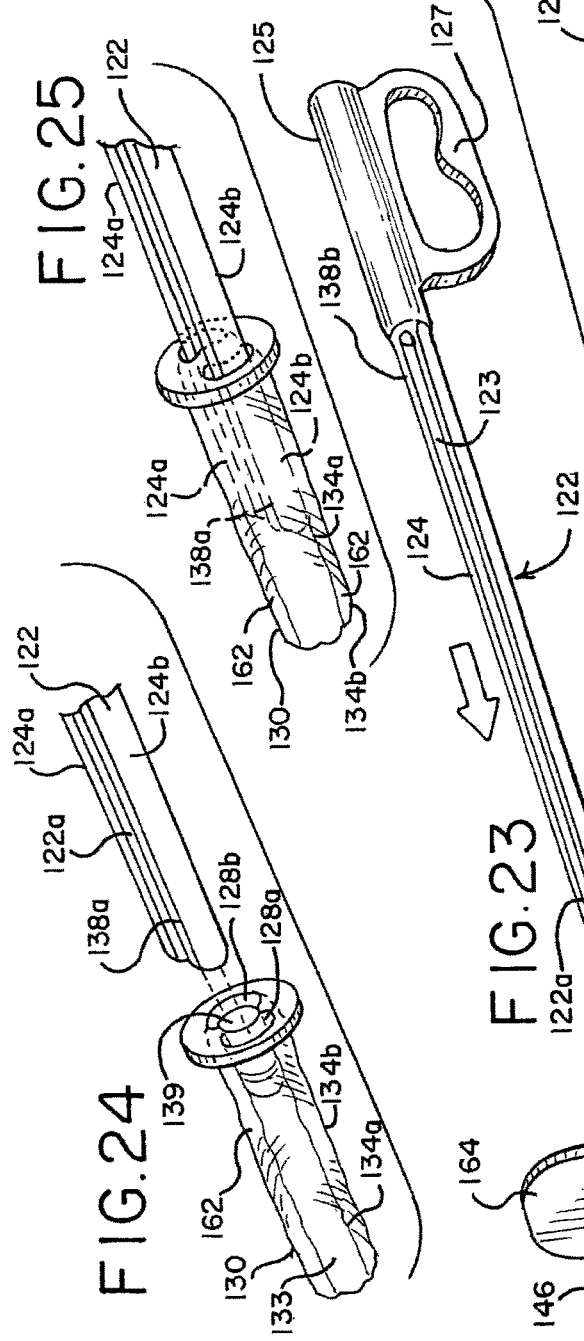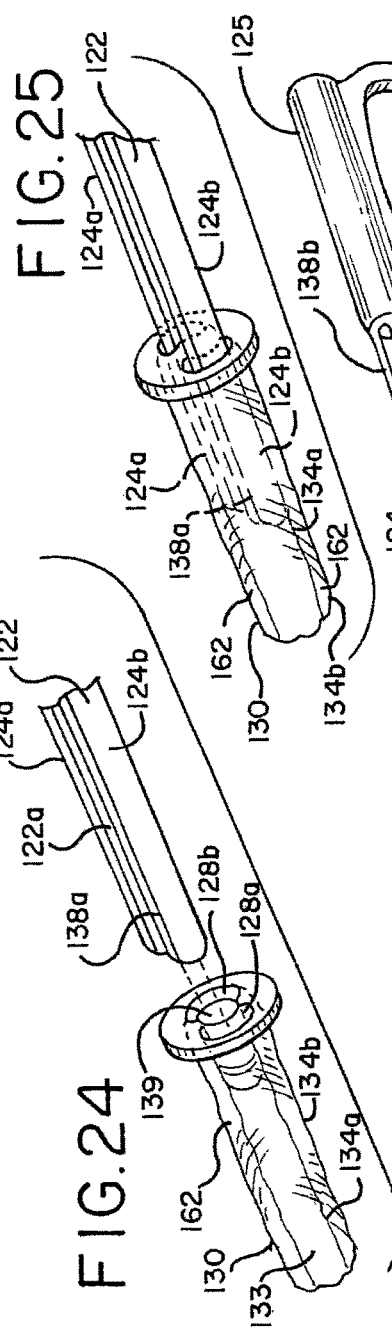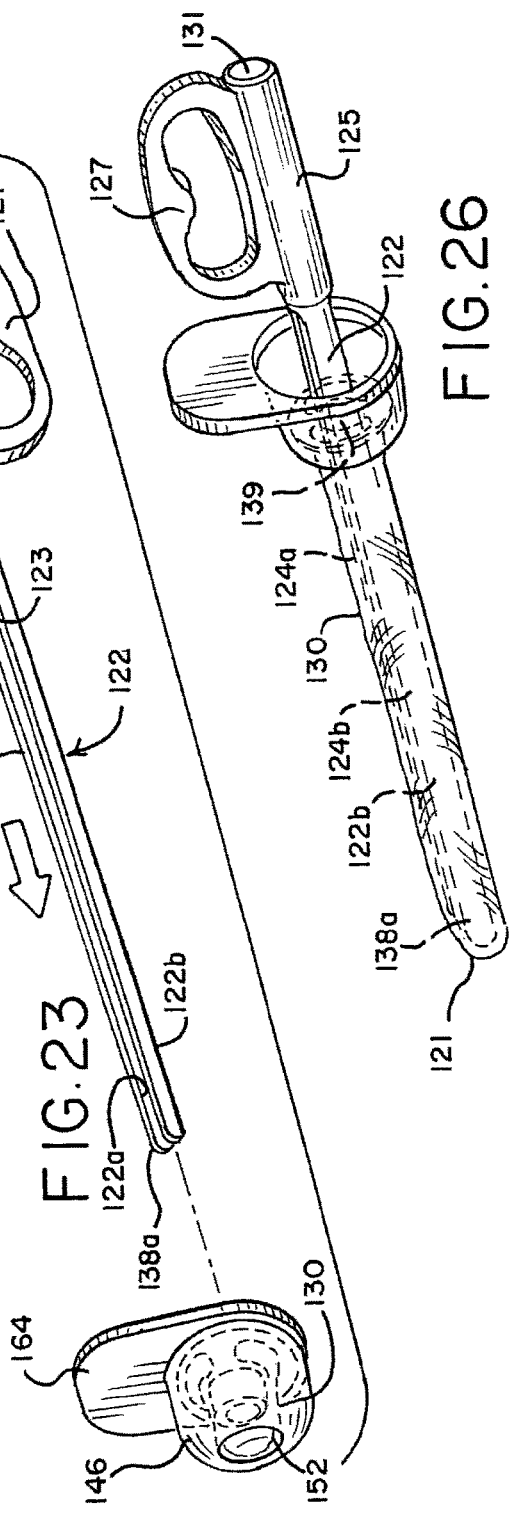

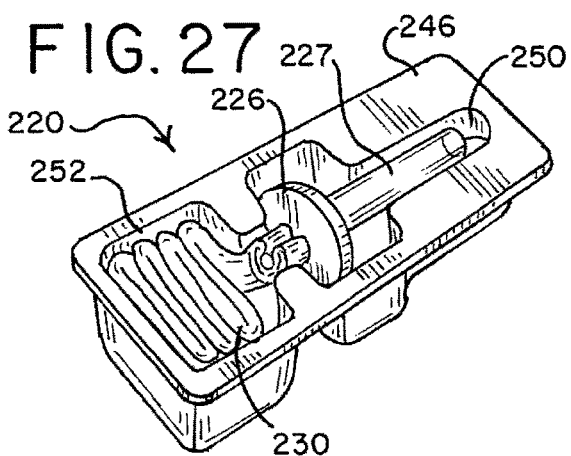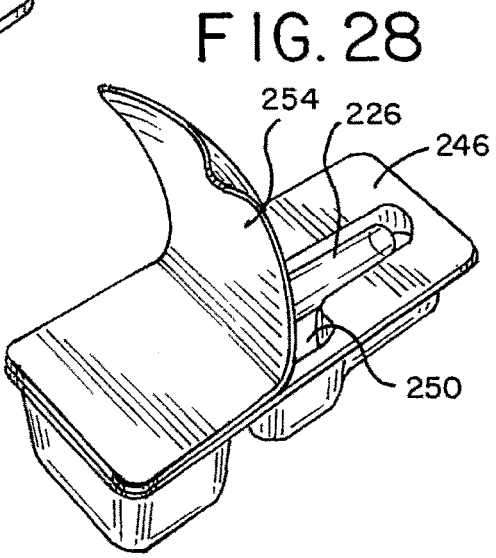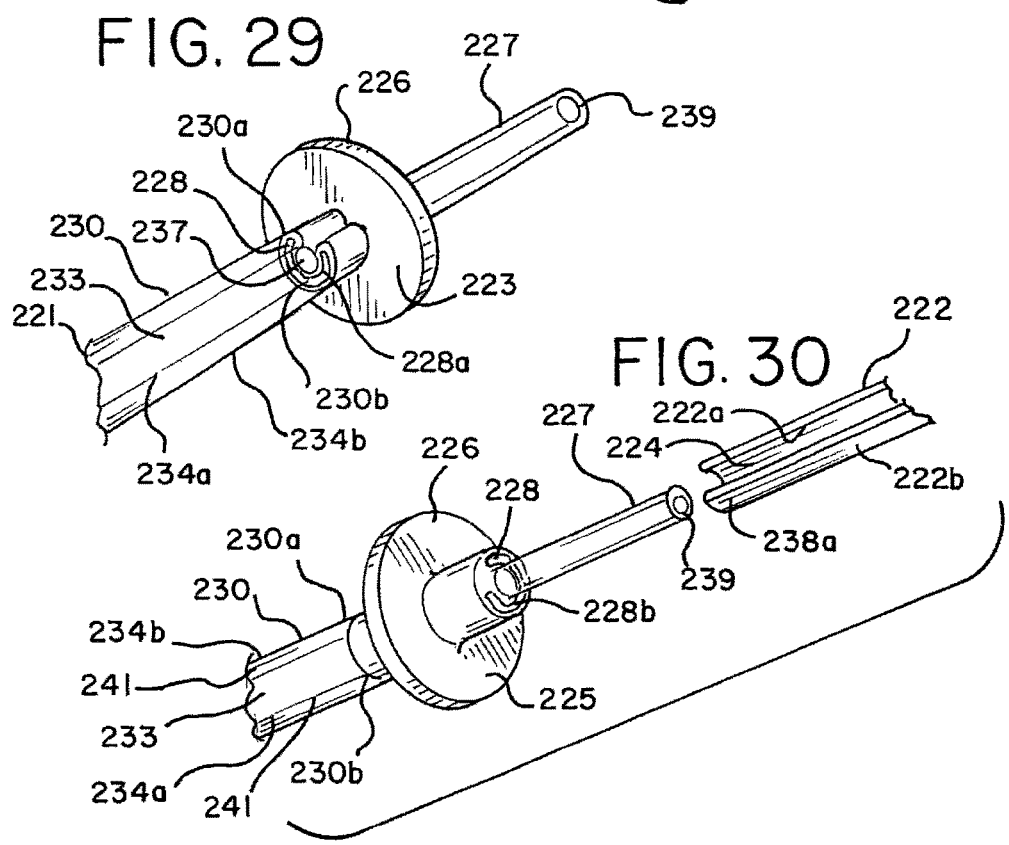

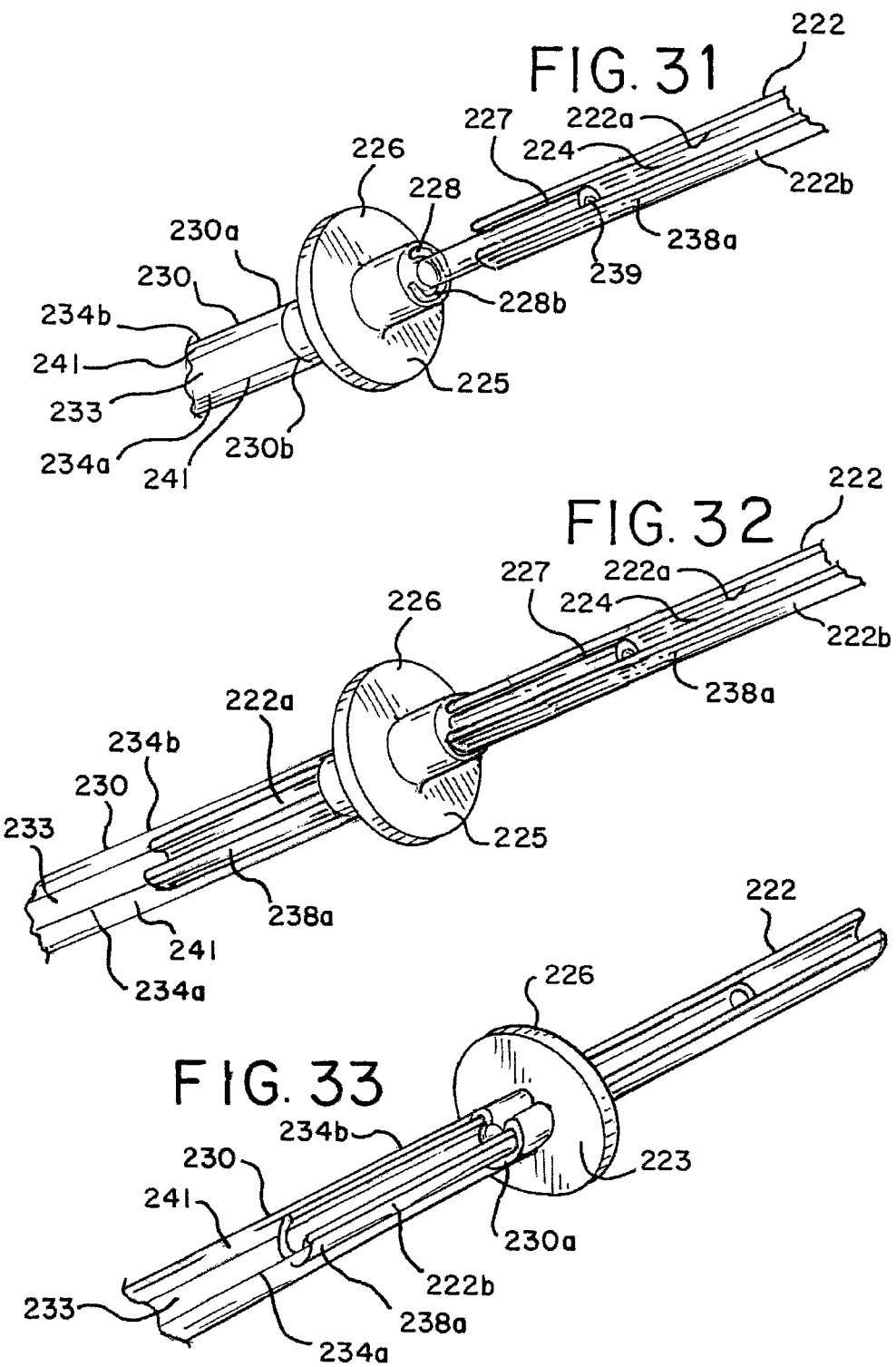

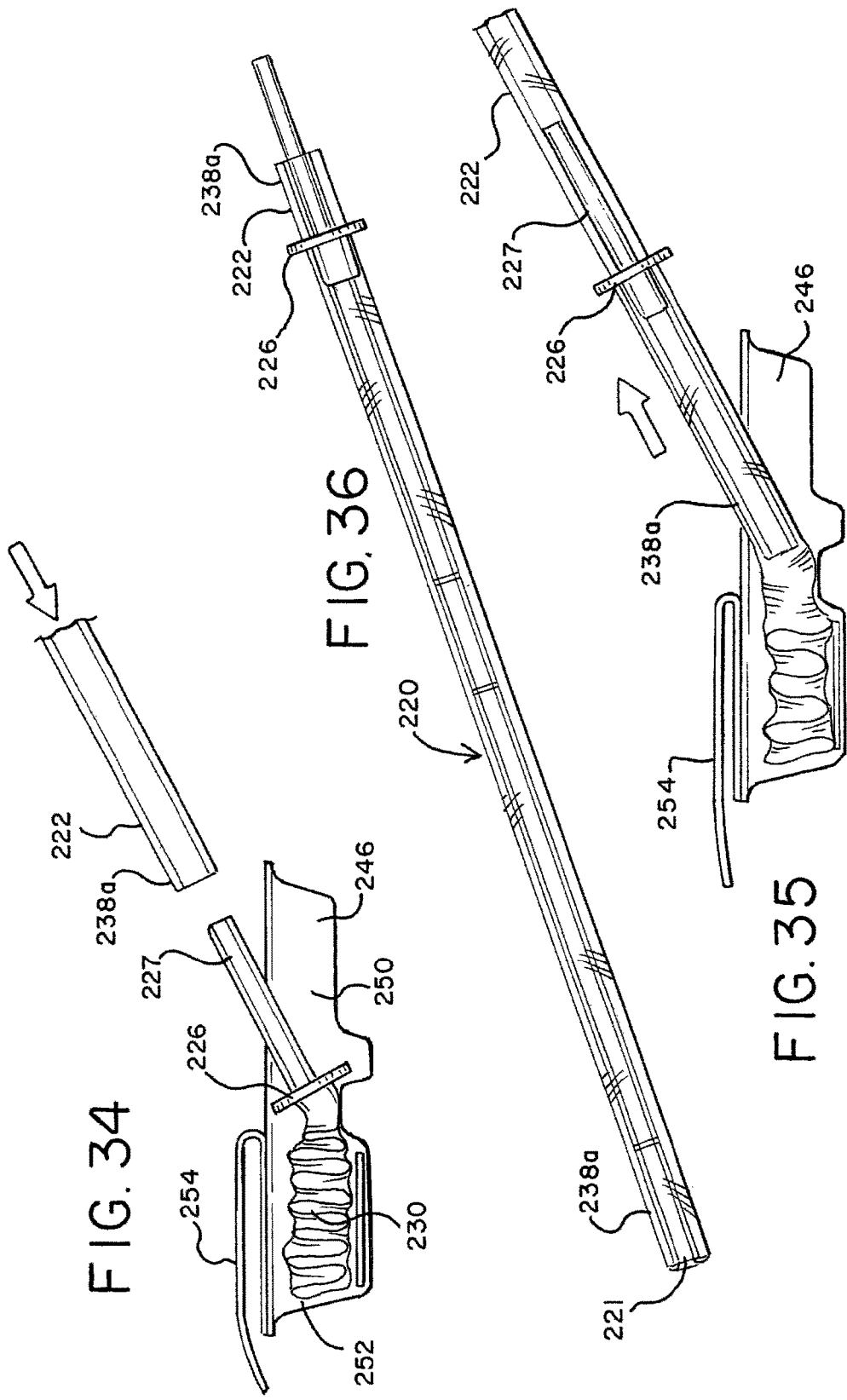

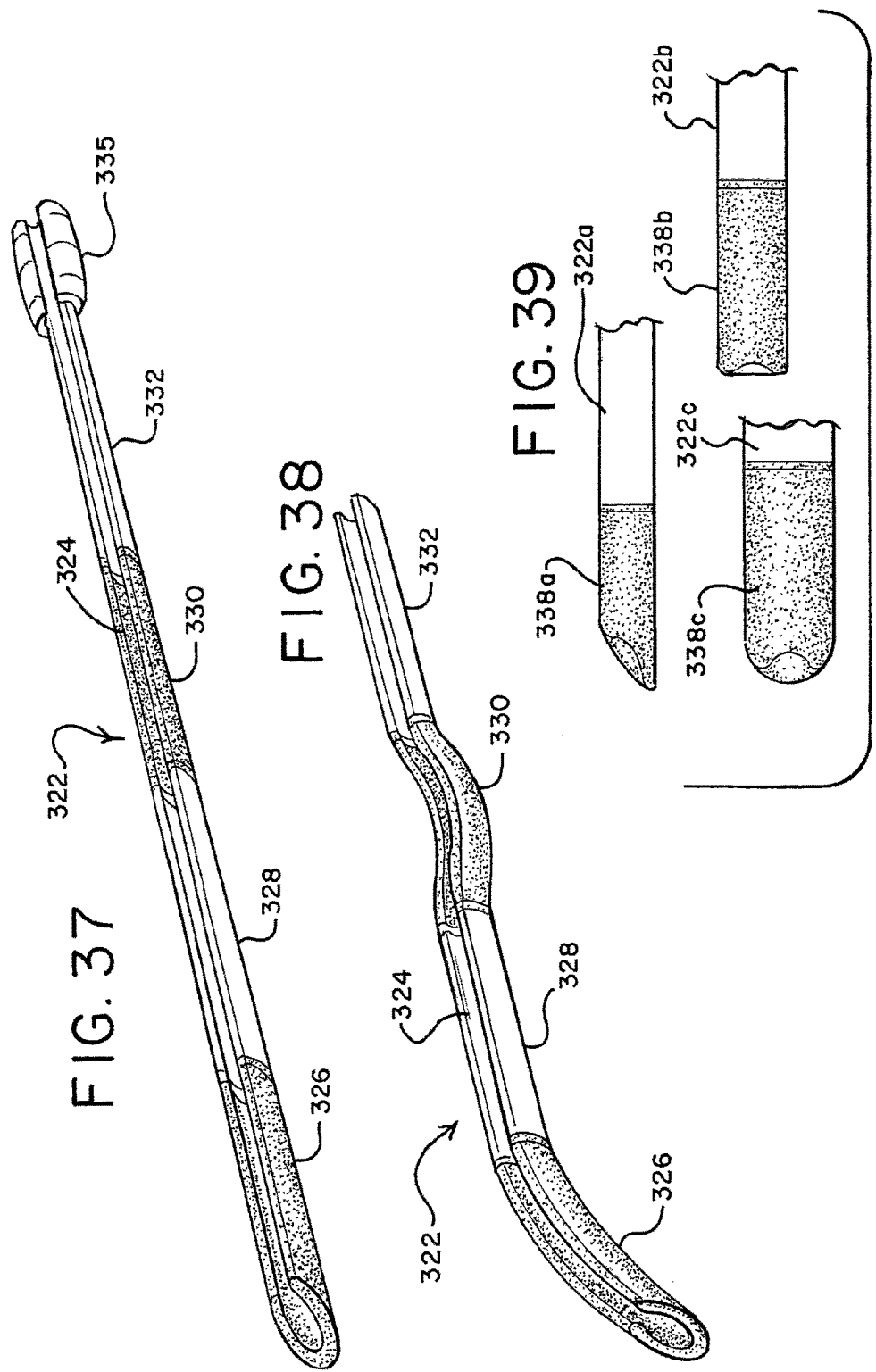

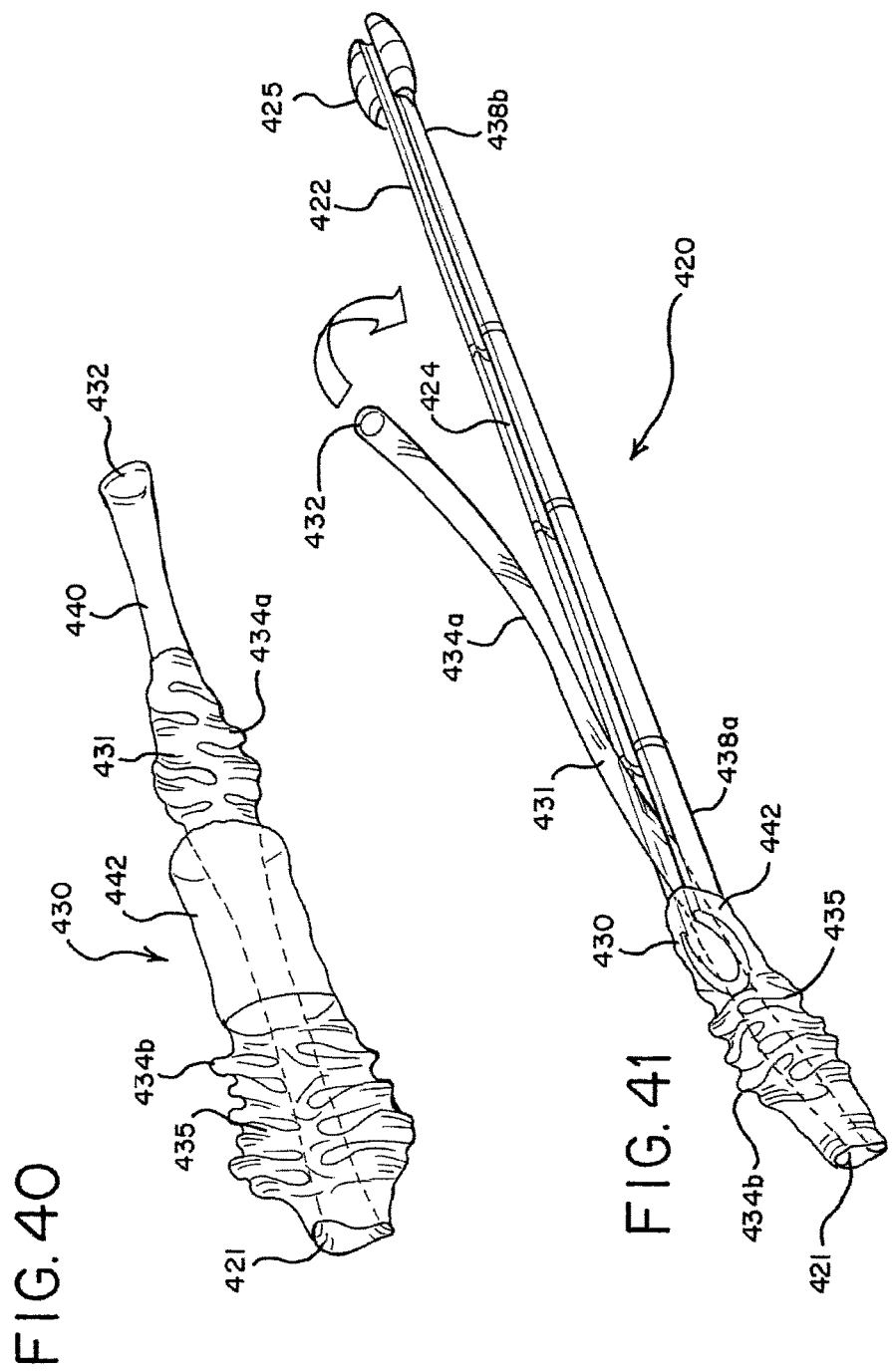

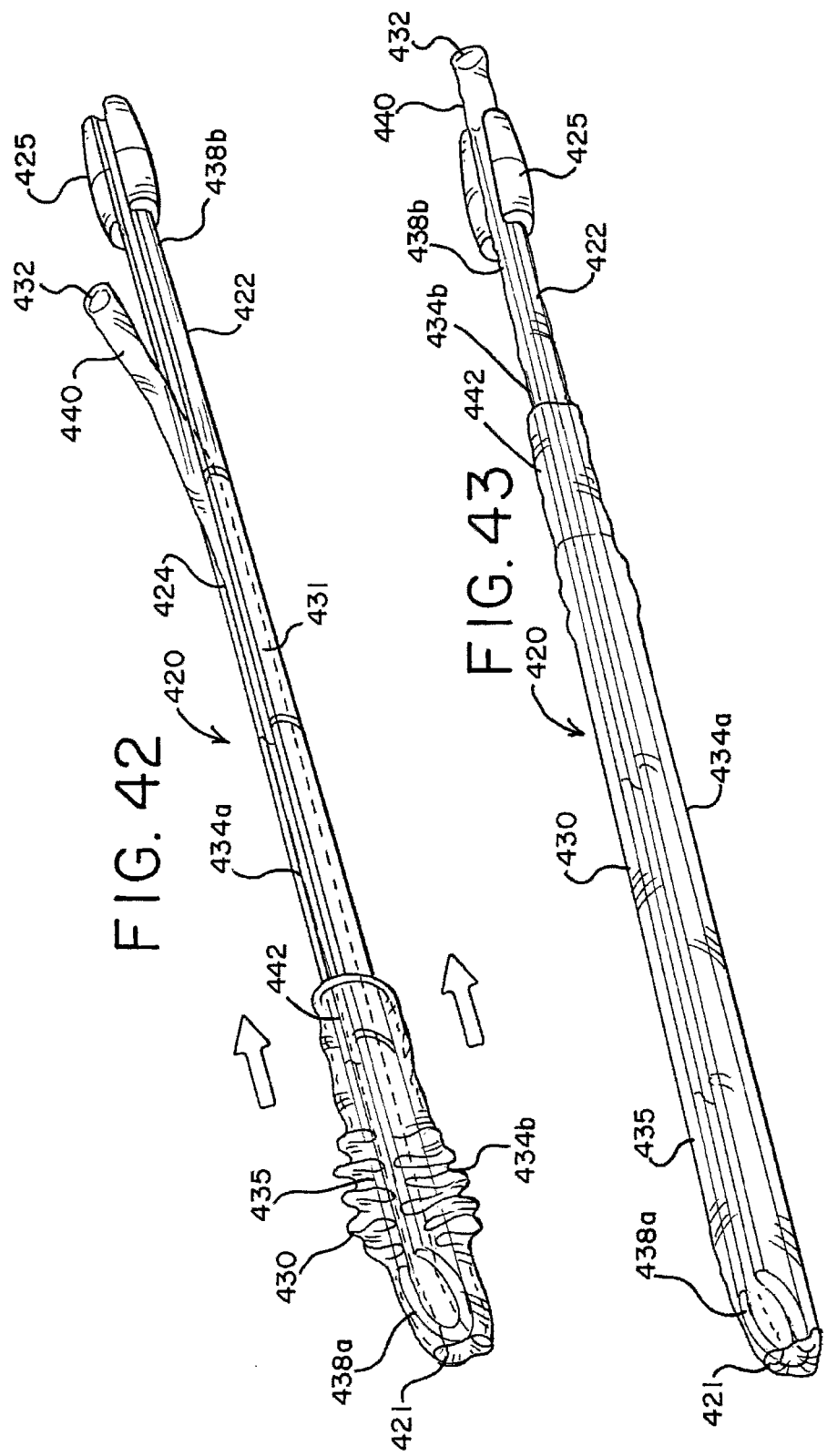

INTERMITTENT CATHETER ASSEMBLY AND KIT

RELATED APPLICATION

This application is a U.S. National Stage of PCT International Patent Application No. PCT/US2013/031230, filed Mar. 14, 2013, which claims the benefit of and priority to U.S. Provisional Patent Application Ser. No. 61/725,311, filed Nov. 12, 2012, both of which are incorporated by reference herein.

FIELD OF THE DISCLOSURE

The present disclosure is generally directed to an intermittent catheter assembly adapted for a user to insert the catheter through the urethra to drain urine from the bladder and, more particularly, to an intermittent catheter assembly and kit with a reusable insertion component for use with a single-use, component which may be disposable, for example, by flushing it down a toilet.

BACKGROUND OF THE DISCLOSURE

Intermittent catheter assemblies are a good option for many users who suffer from various abnormalities of the urinary system. A common situation is where single-use, packaged, ready-to-use sterile catheters are utilized. An important criterion for single-use, ready-to-use products is that they be entirely user-friendly under a wide variety of different conditions.

Among those requiring intermittent catheterization on a regular and recurring basis are users who lead relatively mobile lives. There has been a continuing need for improved intermittent catheter assemblies for such users so they are able to carry with them the requisite number of catheters in a convenient and discrete manner so as to be able perform self-intermittent catheterization several times per day. However, intermittent catheter assemblies that have been available for self-catheterizing have often been provided in long, narrow bulky packages.

While it is possible in some instances to fold the packages so they can be carried in a pocket, even a single packaged intermittent catheter assembly of this type tends to be quite bulky. It is also the case that such intermittent catheter assemblies do not lend themselves to discrete disposal, and no portion of such intermittent catheter assemblies is reusable. As a result, the freedom self-catheterizing could provide has not been fully achieved due to the absence of suitable products that are disposable in a discrete manner in packages of reduced size.

In addition, existing intermittent catheter assemblies have relatively thick-walled catheter tubes formed of polymeric materials, and they typically have been single-use items that are discarded after they are used one time. As will be appreciated, this presents a significant problem due to the large amount of waste material which is created, especially considering the number of users who perform self-intermittent catheterization multiple times per day.

To provide an intermittent catheter assembly suitable for users having relatively normal mobility, it is important to consider various aspects of self-catheterization. These include providing catheter assemblies that will facilitate i) carrying a supply which is sufficient to permit a user to self-catheterize several times a day, ii) inserting catheter assemblies in a manner which does not compromise sterility, iii) draining urine from the human bladder in an efficient and effective manner, and iv) discretely discarding at least the portion of each of the assemblies through which urine is drained. If these aspects of self-catheterization could be addressed, a person having relatively normal mobility would be better able to live an essentially unrestricted lifestyle.

SUMMARY OF THE DISCLOSURE

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, an intermittent catheter assembly includes an elongated introducer element that has a proximal insertion end and a distal end remote from the proximal insertion end. The elongated introducer element is formed of a flexible material adapted for insertion into a urethra during a catheterization procedure and has at least one slit extending longitudinally along at least a portion thereof. The assembly also includes a sheath having a first end and a second end being inverted relative to the first end of the sheath to define inner and outer sleeve portions and a space therebetween. The inner sleeve portion defines a flow path for urine. The elongated introducer element is disposed in the space defined between the inner and outer sleeve portions. The inner sleeve portion is extendable through the at least one slit of the elongated introducer element so as to be disposed within the elongated introducer element and cover an inner surface of the elongated introducer element. The inner sleeve portion separates the inner surface of the elongated introducer element from the urine flow path. Additionally, the outer sleeve portion extends over an outer surface of the elongated introducer element to separate the outer surface of the elongated introducer element from the urethra.

In another aspect, an intermittent catheter assembly includes an elongated introducer element that has a proximal insertion end and a distal end remote from the proximal insertion end. The elongated introducer element is formed of a flexible material adapted for insertion into a urethra during a catheterization procedure. Additionally, the elongated introducer element has at least one slit extending longitudinally along at least a portion thereof. The assembly also includes an applicator that has an opening for receiving the elongated introducer element and a sheath that has a first end secured to the applicator about the opening. The sheath also has a second end that defines a discharge opening. The second end of the sheath is inverted relative to the first end of the sheath and extends into the opening of the applicator to define inner and outer sleeve portions. Additionally, the inner sleeve portion defines a flow path for urine through the discharge opening. The assembly further includes a holding element that is associated with the second end of the sheath for extending the inner sleeve portion through the at least one slit of the elongated introducer element so as to dispose the inner sleeve portion within the elongated introducer element. The inner sleeve portion covers an inner surface of the elongated introducer element to separate the inner surface of the elongated introducer element from the urine flow path. As the elongated introducer element is inserted through the opening of the applicator, the outer sleeve portion extends over an outer surface of the elongated introducer element to separate the outer surface from the urethra.

In another aspect, an intermittent catheter assembly includes an elongated introducer element that has a proximal insertion end and a distal end remote from the proximal insertion end. The elongated introducer element is formed of a flexible material adapted for insertion into a urethra during a catheterization procedure. The elongated introducer element has at least one slit extending longitudinally along at least a portion thereof. The assembly also includes an applicator that has at least one opening for receiving the elongated introducer element and a drainage lumen for the drainage of urine. The assembly also includes a sheath having a first end and a second end being inverted relative to the first end of the sheath to define inner and outer sleeve portions and a space therebetween. The inner sleeve portion defines a urine flow path. The first end of the sheath is secured to the applicator about the at least one opening of the applicator. The opening of the applicator is in communication with the space defined between the inner and outer sleeve portions. The second end of the sheath is secured to the applicator about the drainage lumen wherein the urine flow path defined by the inner sleeve portion is in fluid communication with the drainage lumen of the applicator. The elongated introducer element is insertable through the opening of the applicator and into the space defined between the inner and outer sleeve portions. The outer sleeve portion extends over an outer surface of the elongated introducer element and the inner sleeve portion extends through the slit and covers an inner surface of the elongated introducer element to separate the inner surface of the elongated introducer element from the urine flow path.

In yet another aspect, an intermittent catheter assembly comprising an elongated introducer element formed of a flexible material adapted for insertion into a urethra during a catheterization procedure. The introducer element has at least one slit extending longitudinally along at least a substantial portion of its length. The catheter assembly also includes an applicator having an opening, and a thin sheath having a first end is secured to the applicator about the opening. The thin sheath also has a second end defining a discharge opening which is inverted relative to the first end of the sheath and extends into the opening in the applicator to define inner and outer sleeve portions. The inner sleeve portion defines a flow path for urine through the discharge opening. The catheter assembly also includes a holding element associated with the second end of the sheath for extending the inner sleeve portion through the slit(s) to be disposed within the introducer element. This serves to separate an inner surface of the introducer element from the urine flow path so the introducer element is never exposed to urine during a catheterization procedure. The applicator receives the introducer element through the opening and extends the outer sleeve portion over an outer surface of the elongated introducer element to separate it from the urethra. Accordingly, the portion of the introducer element which is located within the urethra during a catheterization procedure is entirely covered by the inner and outer sleeve portions of the sheath and is therefore suitable for reuse.

In an exemplary embodiment, the introducer element comprises a tube having a single slit which extends along the entire length thereof from a proximal insertion end to a distal end remote therefrom. The proximal insertion end of the introducer element is advantageously beveled to be at other than a right angle to an axis of the introducer element to aid insertion into a urethra during a catheterization procedure. Preferably, to aid insertion into the urethra, it has been found desirable for the proximal insertion end of the introducer element to be beveled so as to be at an angle of between about 15° and about 30° to an axis of the introducer element.

With regard to the slit extending longitudinally along at least a substantial portion of the length of the elongated introducer element, it may advantageously have a width of between about 1.0 mm and 1.5 mm. As for the applicator, it may suitably comprise a collar generally surrounding the first end of the thin sheath and also defining a stop during insertion of the elongated introducer element into a urethra.

As for the holding element, it may advantageously comprise a cord having a first end which is attached to the second end of the thin sheath, and the cord may also have a second end with a finger grip tab attached thereto. In an alternative embodiment, the second end of the thin sheath is secured to generally diametrically opposed portions of the applicator to define the holding element which is associated with the first end of the sheath. In this embodiment, the introducer element has a pair of opposed slits extending longitudinally along a substantial portion of the introducer element from a proximal insertion end toward a distal end thereof.

Still other features and advantages of the present disclosure will become apparent from the following specification taken in conjunction with the accompanying drawings.

BRIEF DESCRIPTION OF THE DRAWINGS

FIG. 4 is a perspective view of the catheter assembly of FIG. 3 in which the catheter assembly is ready for insertion into the urethra to perform a catheterization procedure;

FIG. 5 is a perspective view of the catheter assembly of FIG. 4 in which the inner and outer sleeve portions are being removed from the introducer element for disposal;

FIG. 6 is a perspective view of an intermittent catheter assembly kit in a package containing an introducer element and a plurality of individually packaged sheaths;

FIG. 12 is a schematic view of the inner and outer sleeves of the thin sheath of FIG. 9 before extending them by inserting the introducer element into the open space between them;

FIG. 13 is a perspective view of an applicator, sheath and holding element for the intermittent catheter assembly of FIG. 9 with a peel-off lid being removed therefrom;

FIG. 14 is a perspective view of the applicator, sheath and holding element after the peel-off lid has been removed therefrom ready for insertion of the introducer element;

FIG. 15 is a perspective view of a package containing an introducer element and a plurality of individually packages each containing an applicator, sheath and holding element;

FIG. 16 is an exploded perspective view of another catheter assembly of the present disclosure;

FIG. 17 is a partial perspective view of the applicator and sleeve of FIG. 16;

FIG. 18 is another partial perspective view of the applicator and sleeve of FIG. 16 shown for another direction;

FIG. 23 is perspective of the catheter assembly of FIG. 16 shown prior to insertion of the introducer element into the package;

FIGS. 24 and 25 are partial perspective views showing the introducer element of FIG. 16 being inserted into the applicator and sleeve;

FIG. 26 is a perspective view of the catheter assembly of FIG. 16 shown with the introducer element inserted into the applicator and sleeve;

FIGS. 27 and 28 are perspective views of another embodiment of an applicator and sleeve shown within a package;

FIG. 29 is a perspective view of the applicator shown in FIG. 27;

FIGS. 30-33 are partial perspective views showing an introducer element being inserted into the applicator of FIG. 27;

FIGS. 34 and 35 are perspective view showing an introducer element being inserted into the applicator with the package shown in FIG. 27;

FIG. 36 is perspective view of the introducer element fully inserted into the applicator and sleeve of FIG. 27;

FIGS. 37 and 38 are perspective views of another embodiment of an introducer element of the present disclosure;

FIG. 39 is a plan view of exemplary proximal insertion ends of the introducer element of FIGS. 37 and 38;

FIG. 40 is a perspective view of another embodiment of a sleeve of the present disclosure; and FIGS. 41-43 are perspective views of showing an introducer element being inserted into the sleeve of FIG. 40.

DETAILED DESCRIPTION OF THE DISCLOSURE

Figure 1:
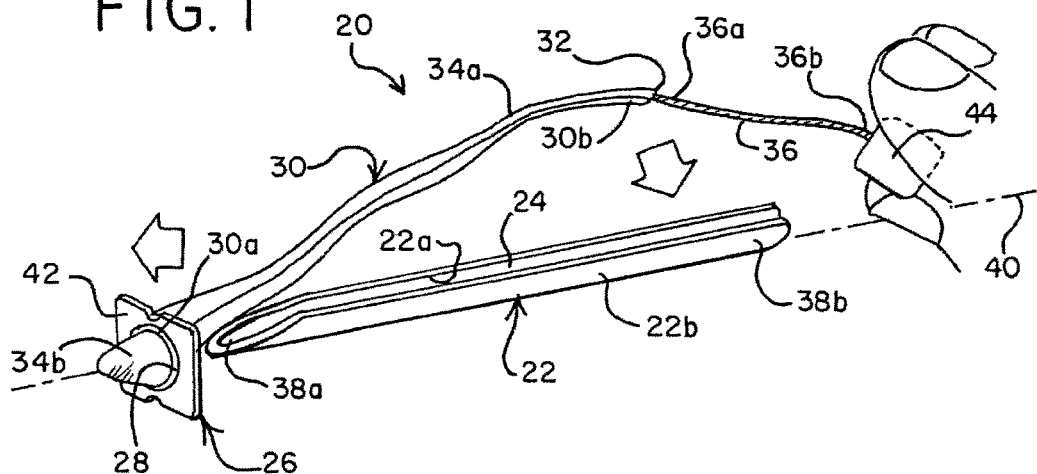
FIG. 1 is a perspective view of an intermittent catheter assembly including an introducer element, an applicator, and a thin sheath in accordance with the present disclosure.
Figure 2:
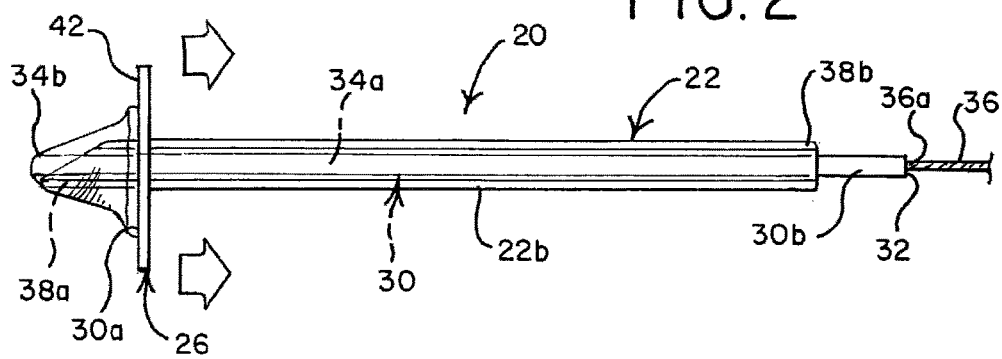
FIG. 2 is a front elevational view of the catheter assembly of FIG. 1 with an inner sleeve portion of the sheath extended through a slit and disposed within the introducer element.
Figure 3:
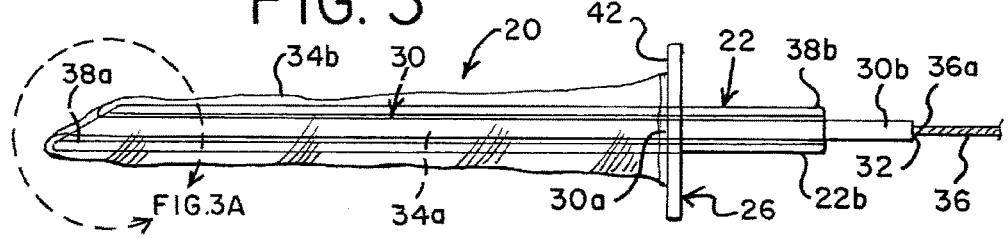
FIG. 3 is a front elevational view of the catheter assembly of FIG. 1 with an outer sleeve portion of the sheath extended over an outer surface of the introducer element in a use position.
Figure 3A:
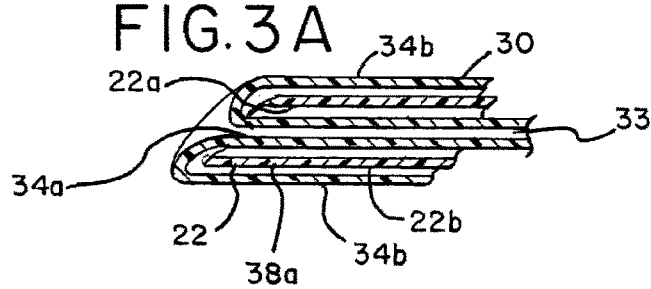
FIG. 3A is an enlarged cross-sectional taken from the area within circle 3A of FIG. 2.

In the illustrations given, and first with reference to FIGS. 1-5, the reference numeral 20 designates generally an intermittent catheter assembly comprising an elongated introducer element 22 which may be formed of a flexible material and is adapted for insertion into a urethra during a catheterization procedure. The introducer element 22 has at least one slit 24 extending longitudinally along a portion of its length and preferably at least a substantial portion of its length. The catheter assembly 20 also includes an applicator generally designated 26 which has an opening 28, and a thin sheath, sleeve or shroud 30 having a first end 30a is secured to the applicator 26 about the opening 28. The thin sheath 30 also has a second end 30b defining a discharge opening 32 which is inverted relative to the first end 30a of the sheath 30 and extends into the opening 28 in the applicator 26 to define inner 34a and outer 34b sleeve portions. The inner sleeve portion 34a defines a flow path 33 (as illustrated in FIG. 3A) for urine through the discharge opening 32. The catheter assembly 20 also includes a holding element 36 associated with the second end 30b of the sheath 30 for extending the inner sleeve portion 34a through the slit(s) such as 24 to be disposed within the introducer element 22. This serves to separate an inner surface 22a of the introducer element 22 from the urine flow path so the introducer element 22 is never exposed to urine during a catheterization procedure. The applicator 26 receives the introducer element 22 through the opening 28 and extends the outer sleeve portion 34b over an outer surface 22b of the elongated introducer element 22 to separate it from the urethra. Referring to FIG. 3A, sleeve 30 everts over the proximal insertion end 38 of introducer element 22 so that the outer sleeve portion 34b extends over outer surface 22b and inner sleeve portion 34a extends over inner surface 22a of introducer element 22. Accordingly, the portion of the introducer element 22 which is located within the urethra during a catheterization procedure is entirely covered by the inner 34a and outer 34b sleeve portions of the sheath 30 and is therefore suitable for reuse, as shown in FIG. 3A.

In an exemplary embodiment, the introducer element 22 comprises a tube having a single slit 24 which extends along the entire length thereof from a proximal insertion end 38a to a distal end 38b remote therefrom. The proximal insertion end 38a of the introducer element 22 may be beveled to be at other than a right angle to the longitudinal axis 40 of the introducer element 22 to aid insertion into a urethra during a catheterization procedure. To aid insertion into the urethra, it may be desirable for the proximal insertion end 38a of the introducer element 22 to be beveled so as to be at an angle of between about 15° and about 30° to an axis of the introducer element.

With regard to the slit 24 extending along the longitudinal axis 40 for the entire length of the elongated introducer element 22, it may have a width of between about 1.0 mm and 1.5 mm. As for the applicator 28, it may include a collar 42 surrounding the first end 30a of the sheath 30 and the applicator defines a stop during insertion of the introducer element 22 into a urethra.

The holding element 36 may comprise a cord having a first end 36a which is attached to the second end 30b of the thin sheath 30, and the cord 36 may also have a second end 36b with a finger grip tab 44 attached thereto.

The introducer element 22 may be formed of a flexible material and is preferable formed of a flexible, shape-memory material, such as a flexible shape-memory polymer. Introducer element 22 and the other introducer elements disclosed herein may be formed, for example, from polyamides, polyvinylchloride, polypropylene, polyester, polyurethane, polyesterurethane, polyetherurethane, poly(ester-etherurethane), fluoropolymers such as, but not limited to, polyvinylidene difluoride, polyvinylidene fluoride, expanded polytetrafluoroethylene, fluorinated ethylene propylene, perfluroalkoxy and combinations of any of the above listed materials. In one embodiment, the introducer element is constructed from a material that allows the introducer element to be bent into a stowed or compact configuration so that it may be, for instance, coiled and carried in a pocket, if desired, and then changed into a generally straight or slightly curved configuration for use during catheterization.

Figure 7:
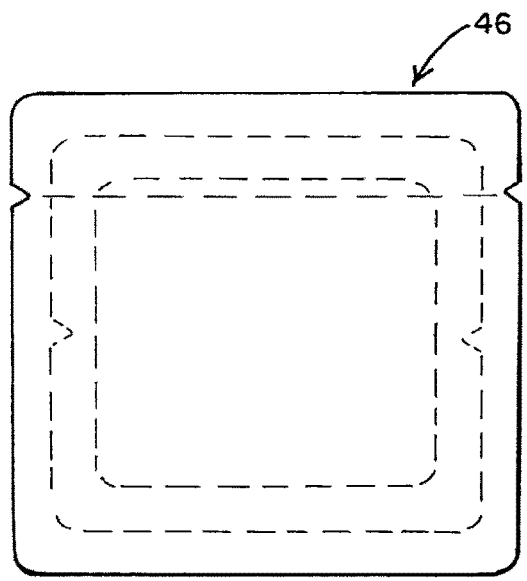
FIG. 7 is a top plan view of a small condom style package containing a single sheath secured to an applicator and having a holding element associated with the sheath.
Figure 7A:
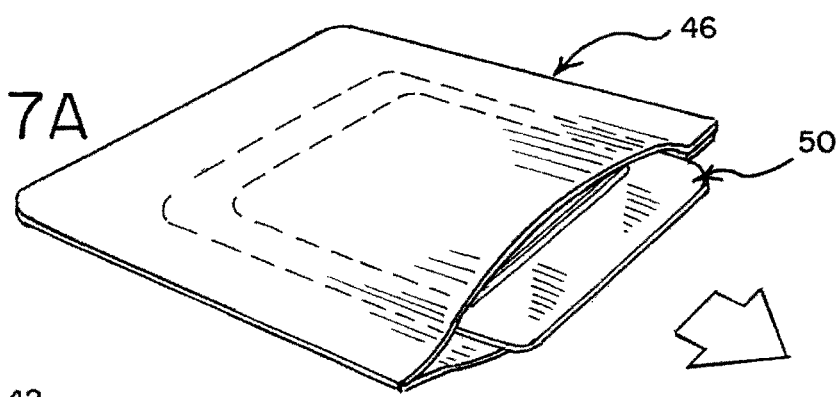
FIG. 7A is a top plan view similar to FIG. 7 illustrating the small condom style package containing a single sheath secured to an applicator after the package has been opened.
Figure 8:
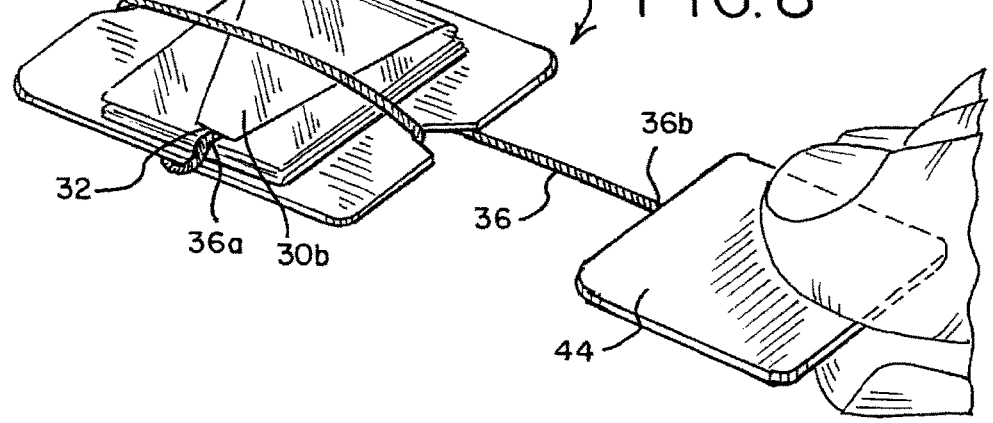
FIG. 8 is a perspective view of a single sheath secured to an applicator and having a holding element associated with the sheath after removal from the package of FIG. 7A.

Introducer element 22 also may be reusable and need not be sterile since the portion inserted into the urethra is entirely covered by the sheath 30 during a catheterization procedure. The applicator 26, thin sheath 30, and holding element 36 may be made of biodegradable materials and, preferably, flushable biodegradable materials. Applicator 26, thin sheath 30, and holding element 36 may be provided in a package 46, which also may be made of biodegradable materials, in a sterile condition for immediate use when removed (see FIGS. 7, 7A and 8). The other applicators, thin sheaths and packaging described herein also may be made of such biodegradable materials. Additionally, introducer element 22 and the other introducer elements described herein also may be made from such biodegradable materials, preferably flexible biodegradable materials and, more preferably, flexible shape-memory, biodegradable materials.

With regard to the foregoing, the biodegradable materials for forming the applicator 26, the thin sheath 30, the holding element 36, introducer element 22 and package 46 may comprise any of a wide range of materials that are flushable for ease of disposal after use. Potential biodegradable polymers include, but are not limited to: polyalkenedicarboylates, poly(alkylcyanoacrylate), polyamides, polyamide-enamines, polyanhydrides, poly(ε-caprolactone), polyesters, polyesterurethane, polyetherurethane, poly(ester-etherurethane), polyglycolide, polyhydroxyalkanoates, polyhydroxybutyrate, poly(hydroxybutyrate-co-valerate), polylactide, poly(p-dioxanone), poly(trimethylene carbonate), polyureas, polyurethane, cellulose, chitin, chitosan, collagen, corn, lignin, soy protein, starch, succinic acid and sugar cane. The flushable material could also be a segmented polymer; a non-degradable polymer mixed with any of the above listed biodegradable polymers, so that at least the sheath 30 would eventually decompose into small pieces.

By providing the applicator 26, the thin sheath 30, and the holding element 36 in a package 46, it is possible to provide a flushable intermittent catheter assembly kit 48 (see FIG. 6) having a reusable elongated introducer element 22, and a plurality of flushable catheter elements 50 each comprising one of the packages 46. As discussed above, each of the packages 46 includes a single, sterile ready-to-use catheter element 50 which is comprised of an applicator 26, thin sheath 30, and holding element 36. As shown in FIG. 6, the kit 48 may comprise a semi-rigid carrying case 52 formed of a paperboard material to have an openable top 52a, a holder 52b for the elongated introducer element 22, and a pocket 52c for, by way of example, a dozen ready-to-use catheter elements 50 with four of each disposed in three adjacent rows within the pocket 52c.

In an alternative embodiment illustrated in FIGS. 9-12, the second end 30b' of the thin sheath 30' may be secured to generally diametrically opposed portions 46a and 46b of the applicator 26' to define the holding element which may be associated with the second end 30b' of the sheath 30'. With this embodiment which is discussed in detail below, the introducer element 22' includes a pair of opposed members or arms 24a' and 24b' each extending parallel to the longitudinal axis 40' of the introducer element 22' from a proximal insertion end 38a' toward a distal end 38b' thereof. Arms 24a' and 24b' define a slit or gap 23', and preferably a planar slit or gap, therebetween.

As with the earlier embodiment, the applicator 26' has an opening 28', and the first end 30a' of the thin sheath 30' may be secured to the applicator 26' about the opening 28'. The second end 30b' of the thin sheath 30' defines a discharge opening 32' which may be inverted relative to the first end 30a' of the sheath 30' and extends into the opening 28' in the applicator 26' to define inner 34a' and outer 34b' sleeve portions. The inner sleeve portion 34a' defines a flow path 33' (shown in FIG. 10A) for urine through the discharge opening 32'. The catheter assembly 20 'also may include a holding element 36' (see FIG. 14) associated with the second end 30b' of the sheath 30' for the inner sleeve portion 34a' to be extended through the slit 23' defined by arms 24a' and 24b' such that inner sleeve portion 34a' is disposed within the introducer element 22'. This serves to separate inner surfaces 22a' of arms 24a'/24b' of the introducer element 22' from the urine flow path so the introducer element 22' is never exposed to urine during a catheterization procedure. The applicator 26' receives the introducer element 22' through the opening 28' and extends the outer sleeve portion 34b' over an outer surface 22b' of the elongated introducer element 22' to separate it from the urethra. Referring to FIG. 10A, sleeve 30' everts over the proximal insertion end 38' of introducer element 22' so that the outer sleeve portion 34b' extends over outer surface 22b' and inner sleeve portion 34a' extends over inner surface 22a' of introducer element 22'. Accordingly, the portion of the introducer element 22' which is located within the urethra during a catheterization procedure is entirely covered by the inner 34a' and outer 34b' sleeve portions of the sheath 30' and is therefore suitable for reuse.

The introducer element 22' comprises a pair of opposed elements or arms 24a' and 24b' which extend longitudinally and define a slit 23' that extends along at least a portion of the introducer element 22' and preferably from the proximal insertion end 38a' toward the distal end 38b' of introducer element 22'. The portion of the arms 24a' and 24b' near the proximal insertion end 38a' of the introducer element 22' may be rounded, as will be appreciated by referring to FIG. 11, which will facilitate insertion into a urethra during a catheterization procedure. The elongated introducer element 22' may include a pair of gripping elements 54a and 54b associated with the distal end 38b' remote from the proximal insertion end 38a' beyond slit 23' (see FIGS. 9-11).

Figure 9:
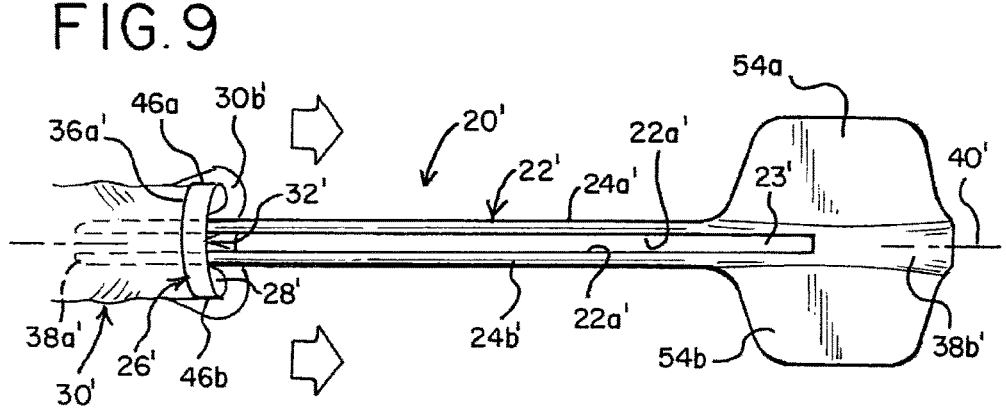
FIG. 9 is a front elevational view of an alternative embodiment of an intermittent catheter assembly with an inner sleeve portion of a sheath being extended through a pair of slits in an introducer element and an outer sleeve portion being disposed over the introducer element.
Figure 10:
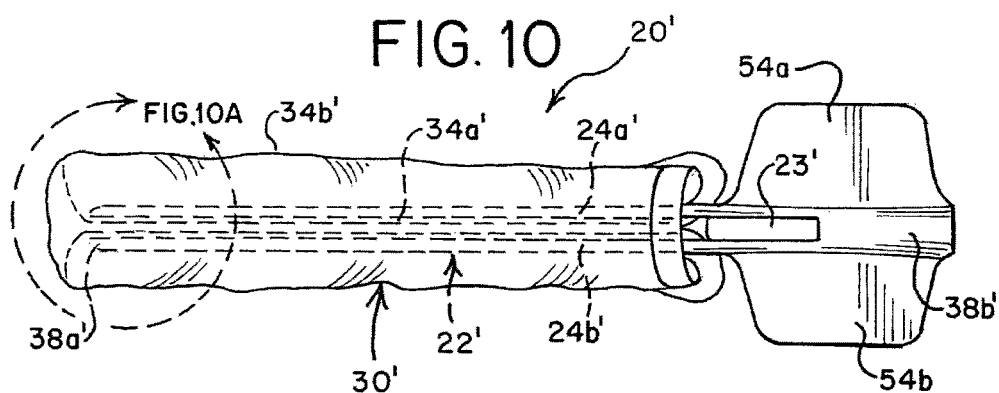
FIG. 10 is a front elevational view of the alternative embodiment of the intermittent catheter assembly of FIG. 9 with the inner and outer sleeve portions disposed in a use position.
Figure 10A:
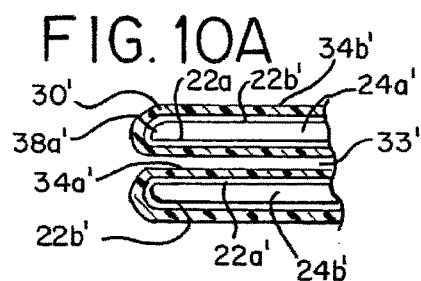
FIG. 10A is an enlarged cross-sectional view taken from the area within circle 10A in FIG. 10.
Figure 11:
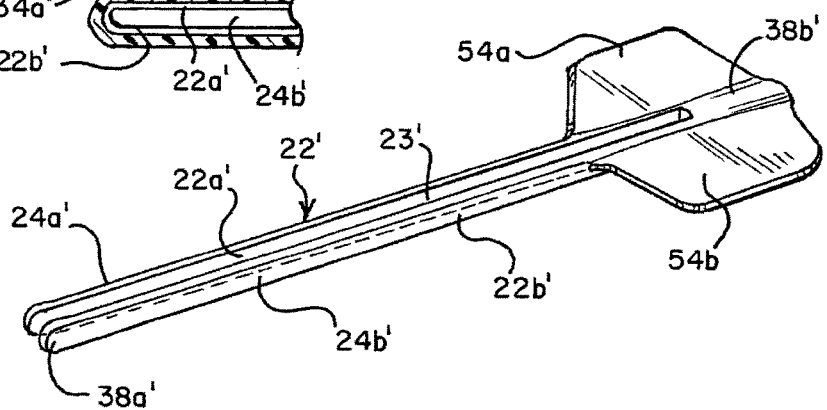
FIG. 11 is a perspective view of the introducer element of FIG. 9 illustrating the pair of slits diametrically opposed within and along a substantial portion of a tube.
Figure 19:
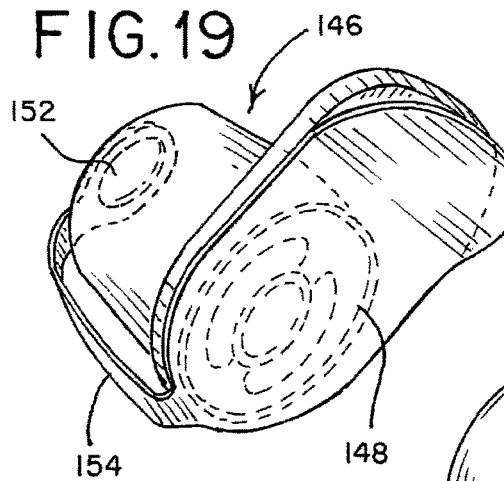
FIGS. 19 and 20 are perspective views of the package shown in FIG. 16.
Figure 20:
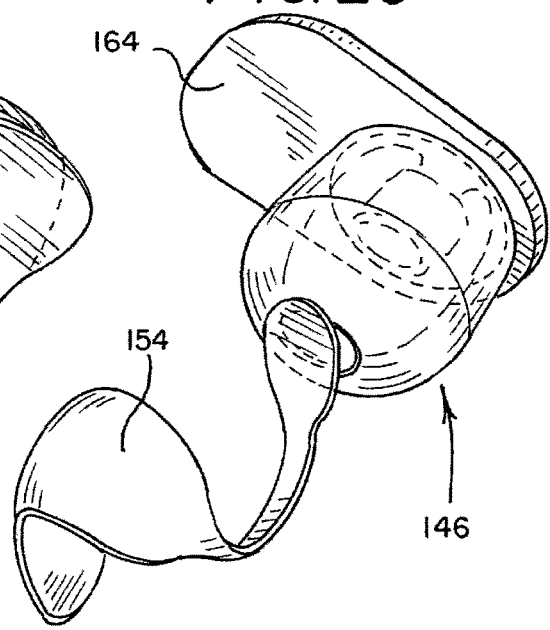
Figure 21:
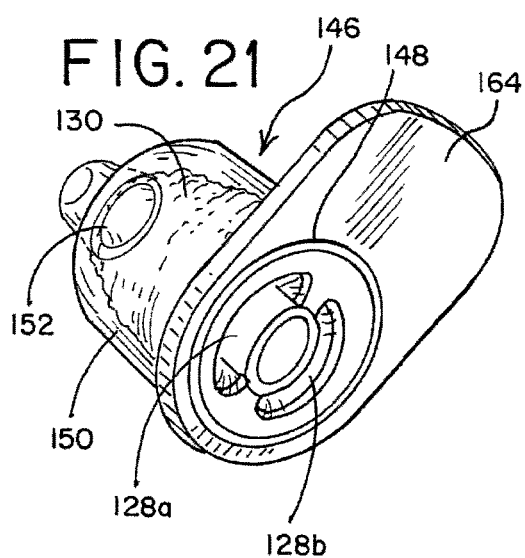
FIGS. 21 and 22 are perspective views of the package of FIG. 16 shown with the applicator and sleeve therein.
Figure 22:
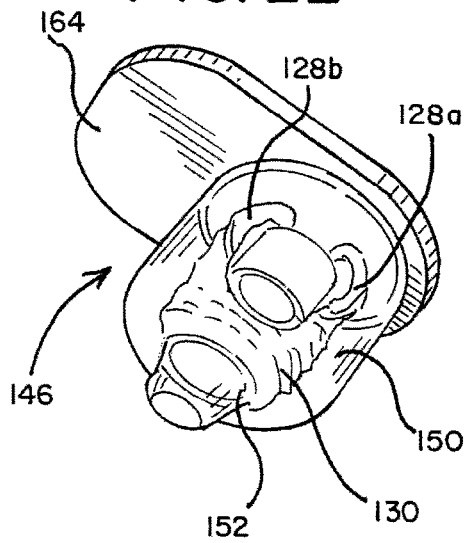

In addition to the foregoing, the introducer element 22' in the embodiment illustrated in FIGS. 9-11 may be formed of a flexible, shape-retaining material such as any of the materials described above with respect to introducer element 22 so it can be coiled and carried in a pocket, if desired. As before, the introducer element 22' is reusable and need not be sterile since the portion inserted into the urethra is entirely covered by the sheath 30' during a catheterization procedure. Also, as before, the applicator 26', the thin sheath 30', and the holding element 36' may be made of flushable biodegradable materials and provided in a package 46' in a sterile condition for immediate use when removed (see FIGS. 13 and 14).

By providing the applicator 26', the thin sheath 30', and the holding element 36' in a package 46', it is possible to provide a flushable intermittent catheter assembly kit 48' (see FIG. 15) having a reusable elongated introducer element 22', and a plurality of flushable catheter elements 50' each comprising one of the packages 46'. Each of the packages 46' includes a single, sterile ready-to-use catheter element 50' which is comprised of an applicator 26', thin sheath 30', and holding element 36'. As shown in FIG. 15, the kit 48' may comprise a semi-rigid carrying case 52' formed of paperboard material with an openable top 52a', a holder (not shown) for the introducer element (not shown), and a pocket 52c' for, e.g., fifteen packages 46' of ready-to-use catheter elements (not shown), i.e., three each in five adjacent rows in the pocket 52c'.

In use of the embodiment illustrated in FIGS. 1-5, it will be appreciated that one of the catheter elements 50 is first removed from one of the packages 46 after it has been opened (FIG. 7A), following which the grip tab 44 is used to extend the inner sleeve portion 34a of the sheath 30 while gripping the collar 42. When this has been done, the slit 24 is used to locate the inner sleeve portion 34a within the introducer element 22 (see FIGS. 1 and 2). After the inner sleeve portion 34a of the sheath 30 has been located within the introducer element 22 (see FIG. 2), the collar 42 is used to extend the outer sleeve portion 34b over a substantial portion of the outer surface 22b of the introducer element 22 to be inserted into the urethra (see FIGS. 3 and 4).

Following a catheterization procedure, the collar 42 and the grip tab 44 can again be used to remove the sheath 30 from the introducer element 22 (see FIG. 5), and the catheter element 50 comprised of the applicator 26, the sheath 30 and the grip tab 44 can be flushed down the toilet and the introducer element put away for use at a later time with a fresh new catheter element 50.

In use of the embodiment illustrated in FIGS. 9-11, 13 and 14, it will be appreciated that one of the catheter elements 50' is first accessed by peeling open one of the packages 46' as shown in FIG. 13. When this has been done, the arms 24a' and 24b' of introducer element 22' are inserted through the opening 28' in the applicator 26' with the two arm portions of the disposed on opposite sides of the inner sleeve portion 34a' which is attached at generally diametrically opposed portions 46a and 46b of the applicator 26' so the inner sleeve portion 34a' is within the introduce element 22'. Next, the introducer element 22' is fully inserted through the opening 28' in the applicator 26' causing the inner sleeve portion 34a' and the outer sleeve portion 34b' to be fully deployed (see FIG. 10).

Referring to FIG. 12, it will be noted that there are openings 56a and 56b into which the two arm portions 24a' and 24b' of the introducer element 22' can be inserted. As shown, the two arms 24a' and 24b' are disposed on opposite sides of the inner sleeve portion 34a' and, as noted above, the inner sleeve portion 34a' is attached at generally diametrically opposed portions 46a and 46b of the applicator 26'. When the introducer element 22' is further inserted, it causes the inner sleeve portion 34a' and the outer sleeve portion 34b' of the sheath 30' to "unfold" or "unroll" to cover the inner and outer surfaces 22a' and 22b'.

In the position shown in FIG. 10, the gripping elements 54a and 54b can be used to insert the catheter assembly 20' into the urethra for a catheterization procedure. After a catheterization procedure, the introducer element 22' can be removed from the catheter element 50', and the catheter element 50' comprised of the applicator 26', the sheath 30', and the holding element 36', can be removed from the package 46' which is preferably formed of plastic in the form of, e.g., a contact lens case. The catheter element 50' can then be flushed down the toilet, the plastic package 46' discarded, and the introducer element 22' put away for later use.

FIGS. 16-26 illustrate another embodiment of an intermitted catheter assembly 120 comprising an elongated introducer element 122, an applicator 126 and a package 146. Similar to elongated introducer element 22', introducer element 122 includes a pair of opposed members or arms 124a and 124b each extending parallel to the longitudinal axis of the introducer element 122 from a proximal insertion end 138a toward a distal end 138b thereof. Arms 124a and 124b define a slit or gap 123, and preferably a planar slit or gap, therebetween. At or near the distal end 138b of introducer element 122 is a handle portion 125 which includes a finger or hand gripping member 127 for gripping by a user. Handle portion 125 includes a drainage lumen 129 therethrough which leads to a drainage opening 131 (as best shown in FIG. 26) for the drainage of urine. In addition to the foregoing, the introducer element 122 may be formed of a flexible, shape-retaining material such as any of the materials described above with respect to introducer element 22 so it can be coiled and carried in a pocket, if desired.

As with the earlier embodiments, a sleeve or sheath 130 for covering or shrouding the introducer element 122 is attached to applicator 126. Referring to FIGS. 17 and 18, applicator 126 also has openings 128a and 128b for receiving arms 124a and 124b of introducer element 122. The first end 130a of the sleeve 130 is secured to the applicator 126 about the openings 128a and 128b. As in the previous embodiments, sleeve 130 is inverted at 121 (FIG. 26) such that second end 130b is adjacent or near first end 130a. The second end 130b of sleeve 130 is secured about a drainage lumen 137 of applicator 126, which lumen 137 leads to drainage opening 139 (FIG. 18). In the illustrated embodiment, drainage lumen 137 is defined by a proximally extending stem 135 to which second end 138b of sleeve 130 is connected. The inverted sleeve 130 defines inner 134a and outer 134b sleeve portions. The inner sleeve portion 134a defines a flow path 133 for passage of urine therethrough. Urine passes through flow path 133 defined by inner sleeve portion 134a and through drainage lumen 137 and drainage opening 139 of applicator 126.

Turning to FIGS. 19-22, applicator 126 and sleeve 130, optionally, may be packaged in a package 146. Package 146 includes a first or introducer opening 148 at or near the top of the package 146 wherein the opening 148 receives and retains applicator 126 when applicator 126 and package 146 are discrete individual pieces. In some embodiments, applicator 126 and package 146 may be formed as a single unitary structure. Package 146 defines a cavity 150 that contains sleeve 130 in a stowed or folded configuration. There is a second or deployment opening 152 at or near the bottom of package 146 for deployment of sleeve 130 when introducer element 120 is inserted therein. The package may also include a cover 154 that covers first and second opening 148 and 152. Cover 154 is preferably a peelable foil that is sealed about first and second opening 148 and 152. In the illustrated embodiment cover 154 includes a first portion 156 that covers opening 148 and a second portion 158 that covers opening 152. Cover 154 also includes a section 160 between portions 156 and 158 so that both portions may be removed from the package with a single movement. In the illustrated embodiment, cover 154 is of a one piece construction that extends around package 146 to cover both openings 148 and 152. Other embodiments may include two separate covers wherein each cover covers and seals one of the openings.

In use, cover 154 is removed from package 146 to expose openings 148 and 152. Referring to FIGS. 23-26, introducer element 122 is inserted into applicator 126 and sleeve 130 to deploy sleeve 130 out of opening 152 in the bottom of package 146. In particular and referring to FIGS. 24-26, arms 124a and 124b of introducer element 122 are inserted into and through openings 128a and 128b of applicator 126 and into a space 162 (FIGS. 24 and 25) between inner sleeve portion 134a and outer sleeve portion 134b. Introducer element 122 is advanced through openings 128a and 128b until the proximal insertion portion 138a of introducer element 122 is at the inverted portion 131 (FIG. 26) of sleeve 130 and drainage opening 139 of applicator 126 is aligned and in abutting communication with drainage lumen 129 (FIG. 16) of handle portion 125 of introducer element 122. Inner sleeve portion 134a separates inner surfaces 122a of arms 124a/124b of the introducer element 122 from the urine flow path so that inner surfaces 122a of introducer element 122 are never exposed to urine during a catheterization procedure. Additionally, outer sleeve portion 134b covers outer surfaces 122b of arms 124a/124b of the elongated introducer element 122 to separate them from the urethra. Accordingly, the portion of the introducer element 122 which is located within the urethra during a catheterization procedure is entirely covered by the inner 134a and outer 134b sleeve portions of the sheath or sleeve 130 and is therefore suitable for reuse.

The user may use a gripping portion 164 (FIG. 23) of package 146, such as the illustrated finger tab, and handle 125 of the introducer element 122 to assist in positioning and inserting catheter assembly 120 into the urethra. Catheter assembly 120 is inserted through the urethra until proximal end portion 138a enters the bladder. Urine drains through flow path 133 defined by inner sleeve portion 134a, lumen 137 applicator 126 (FIG. 17), drainage lumen 127 and out of drainage opening 131 of handle 125 into a suitable collection receptacle. After drainage of the bladder is completed, catheter assembly 120 is retracted from the urethra. Introducer element 122 is removed from sleeve 130 and applicator 126. Sleeve 130, applicator 126 and package 146 are then disposed of. In one embodiment, sleeve 130, applicator 126 and package 146 are made of flushable materials that may be disposed of by flushing down the toilet. Such materials may be water soluble or degradable materials. In other embodiments, sleeve 130 and applicator 126 may be made of flushable materials and are separable from package 146. In such embodiments, sleeve 130 and applicator 126 may be disposed of in the toilet and package 146 is disposed of in an appropriate waste collection container. As before, the introducer element 122 is reusable and need not be sterile since the portion inserted into the urethra is entirely covered by the sheath 130 during a catheterization procedure.

FIGS. 27-36 illustrate yet another catheter assembly 220 of the present disclosure. Catheter assembly 220 includes an elongated introducer element 222 (shown in FIGS. 30, 31 and 36), an applicator 226, sleeve 230 and, optionally, a package of 246. Similar to elongated introducer element 22, elongated introducer element 222 may be formed of a flexible material and is adapted for insertion into a urethra during a catheterization procedure. As shown in FIGS. 30 and 31, introducer element 222 has at least one slit 224 extending longitudinally along a portion of its length and preferably at least a substantial portion of its length.

Turning to FIGS. 29-33, applicator 226 includes a first or outer passageway 228 extending through applicator 226 and having proximal opening 228a and a distal opening 228b. A thin sheath, sleeve or shroud 230 has a first end 230a secured to the applicator 226 about proximal opening 228a of passageway 228. As in the previous embodiments, sleeve 230 is inverted about 221 (FIG. 29) such that a second end 230b of sleeve 230 is adjacent or near first end 230a. The second end 230b of sleeve 230 is secured about a drainage passageway 237 of applicator 226. In the illustrated embodiment, passageways 228 and 237 are defined by a proximally extending stem 235 projecting from a proximal surface 223 of applicator 226. Passageway 237 leads to and is in fluid communication with drainage tube 227 distally extending from a distal surface 225 of applicator 226. Drainage tube 227 includes a drainage opening 239.

Inverted sleeve 230 defines inner 234a and outer 234b sleeve portions. Inner sleeve portion 234a defines a flow path 233 for passage of urine therethrough. Urine passes through flow path 233 and through passageway 237, drainage tube 227 and drainage opening 239 of applicator 226.

Turning to FIGS. 30-31, to insert introducer element 222 into applicator 226, drainage tube 227 is aligned and inserted into proximal insertion end 238a of introducer element 222. Drainage tube 227 functions as guide member to align and guide proximal insertion end 238a of introducer element 222 to opening 228b. In the illustrated embodiment, opening 228b has the generally the same profile as introducer element 222. As illustrated in FIGS. 32 and 33, introducer element 222 is inserted through passageway 228 and into the space 241 defined between inner sleeve portion 234a and outer sleeve portion 234b. Introducer element 222 is inserted into passageway 228 until proximal insertion end reaches inverted portion 221 of sleeve 230, as illustrated in FIG. 36. Inner sleeve portion 234a serves to separate and shroud an inner surface 222a (FIGS. 30-33) of the introducer element 222 from the urine flow path so that introducer element 222 is never exposed to urine during a catheterization procedure. Additionally, outer sleeve portion 234b extends over and shrouds an outer surface 222b (FIGS. 30-33) of the elongated introducer element 222 to separate it from the urethra. Accordingly, the portion of the introducer element 222 which is located within the urethra during a catheterization procedure is entirely covered by the inner 234a and outer 234b sleeve portions of the sheath 230 and is therefore suitable for reuse.

Referring to FIGS. 27, 28, 34 and 35, applicator 226 and sleeve 230, optionally, may be packaged in a package 246. Package 246 includes a first cavity 250 for containing applicator 226 and a seconded cavity 252 for containing sleeve 230 in a folded or rolled up condition. The package 246 may include a cover or seal 254 covering the top of the package 246. Preferably, the cover 254 is a peelable seal.

Referring to FIGS. 34 and 35, in use, cover 254 is removed from package 246 and drainage tube 227 is lifted or tilted at an angle by the user. Drainage tube 227 is aligned and inserted into the proximal insertion end 238a of introducer element 222. The introducer element 222 is advanced and guided by drainage tube 227 into distal opening 228b of passageway 228 of applicator 226, as described above. Introducer element 222 is advanced through passageway 228 by the user gripping and pulling applicator 226 along introducer element 222 or by continued insertion of introducer element into passageway 228 with applicator 226 is held stationary. Introducer element 222 is advanced through passageway 228 and through the space 241 between inner and outer sleeve portions 234a/234b until the proximal insertion portion 238a of introducer element 222 reaches inverted portion 221 of sleeve 230 and drainage tube 227 of applicator 226 extends out of distal end portion 238b of introducer element 222, as illustrated in FIG. 36.

The user may grip applicator 226 to assist in positioning catheter assembly 220 and inserting it into the urethra. Catheter assembly 220 is inserted through the urethra until proximal end portion 238a enters the bladder. Urine drains through flow path 231 defined by inner sleeve portion 234a and through passageway 237 and drainage tube 227 of applicator 226. Drainage tube 226 extends beyond the distal end portion 238b of introducer element 222 to reduce the chances of urine coming into contact with the distal end portion 238b of introducer element 222. After drainage of the bladder is completed, catheter assembly is retracted from the urethra. Introducer element 222 is removed from sleeve 230 and applicator 226. Sleeve 230 and applicator 226 are then disposed of. As before, the introducer element 222 is reusable and need not be sterile since the portion inserted into the urethra is entirely covered by the sheath 230 during a catheterization procedure. Also, as before, the applicator 226 and sleeve 230 may be made of flushable biodegradable materials.

FIGS. 37-39 disclose one embodiment of an introducer element 322 of the present disclosure, which may be used with the applicators disclosed herein. Similar to elongated introducer element 22, elongated introducer element 322 may be formed of a flexible material and is adapted for insertion into a urethra during a catheterization procedure. Introducer element 322 has at least one slit 324 extending longitudinally along a portion of its length and preferably at least a substantial portion of its length.

Introducer element 322 also may include different flexibility and stiffness characteristics along its lengths to impart varying flexibility to the introducer element 322. FIGS. 37 and 38 show introducer element 322 divided into four sections, wherein the sections have different flexibilities relative to adjacent sections. Introducer 322 includes a first proximal section 326, a second section 328, a third section 330 and a fourth section 332. The first proximal section 326 is configured to be inserted through the urethra and into the bladder. First section 326 may be relatively more flexible than second section 328. Second section 328 is positioned adjacent to and distally of first section 326 and is relatively more rigid than first section 326. A third section 330 is positioned adjacent and distally of second section 328. Third section 330 is relatively more flexible than second section 328 and fourth section 332, which is positioned distally of third section 330 and relatively more rigid than the third section. As illustrate in FIG. 38, the first and third sections 326 and 330 are flexible while the second and fourth 328 and 332 are substantially rigid and remain generally linear.

The flexibility/rigidity of each section may be varied by varying the type or thickness of the material or by creating flexure areas, such as slits or cut-outs. In some applications, varying the flexibility/rigidity of the introducer along its length assists in inserting and traversing the introducer element and sleeve through the tortuous pathway of the male urethra.

FIG. 39 illustrates some exemplary configurations of the proximal insertion end, generally designated 338, of the introducer element, generally designated 322. For example, element 322a includes an angled proximal insertion end 338a. Introducer elements 322b and 322c include more blunted proximal end insertion ends 338b and 338c, respectively.

FIGS. 40-43 illustrate another embodiment of a catheter assembly 420 of the present disclosure. As illustrated in FIGS. 40 and 41, catheter assembly 420 includes an introducer element 422 and a sheath, sleeve or shroud 430. Sleeve 430 is similar to the other sleeves described above and is formed of a thin material. Sleeve 430 is inverted at 421 to form an inner portion 434a and an outer portion 434b. Inner portion 434a defines a flow path 431 having a drainage opening 432 for the passage of urine therethrough. As will be explained in more detail below, a space 435 for receiving the introducer element 422 is defined between inner 434a and outer 434b portions of sleeve 430.

As shown in FIGS. 41-43, introducer element 422 includes a proximal insertion end portion 438a and a distal end portion 438b. Introducer element 422 also includes a slit 424 at least partially along, and preferably substantially along, the entire length of introducer element 422. A handle 425 may be located at the distal end portion 438b for gripping by the user.

In use, the user inserts proximal insertion end 438a into the space 435 defined between inner portion 434a and outer portion 434b of sleeve 430. The inner portion 434a may include gripping portion 440 designated for gripping the inner portion. Similarly, the outer portion 434b also may have a gripping portion 442 for gripping the outer portion. The gripping portions 440 and 442 may be designated by color or texture. It is preferable for the user to use the gripping portions so that the user recognizes and utilizes the gripping portions of the sleeve to handle the sleeve. Handling the sleeve by the designated gripping portions reduces the risk of contamination of the portion of the sleeve inserted into the urethra because the portions inserted into the urethra are not contacted by the user's fingers.

After the proximal insertion end 438a has been inserted into space 435, inner portion 434a of sleeve 430 is gripped by the user at gripping portion 440 and pulled along the length of introducer element 422. Inner portion 434a is then or simultaneously inserted into slit 424 of introducer element 422. Referring to FIG. 42, outer portion 434b of sleeve 430 is then gripped by gripping portion 442 and pulled along the length of introducer element 422 until outer portion 434b covers the surface of introducer element 422.

The user may grip handle portion 425 of introducer element 422 to insert and advance catheter 420 into and through the urethra. Catheter assembly 420 is inserted through the urethra until proximal end portion 438a enters the bladder. Urine drains through a flow path 431 defined by inner sleeve portion 434a and out of drainage opening 432 into a suitable collection receptacle. Drainage opening 432 is located beyond the distal end portion 438b of introducer element 422 to reduce the chances of urine coming into contact with the distal end portion 438b of introducer element 422. After drainage of the bladder is completed, catheter assembly is retracted from the urethra. Introducer element 422 is removed from sleeve 430 and sleeve 430 is then disposed of. As before, the introducer element 222 is reusable and need not be sterile since the portion inserted into the urethra is entirely covered by the sheath 230 during a catheterization procedure. Also as before, sleeve 430 may be made of flushable biodegradable materials and disposed of in a toilet.

While in the foregoing there have been set forth different embodiments of the disclosure, it will be appreciated that they have been provided for purposes of illustration only and the disclosure is not limited to these embodiments but is only limited to what falls within the scope of the appended claims.

What is claimed is:

1. An intermittent catheter assembly, comprising:
an elongated introducer element having a proximal insertion end and a distal end remote from the proximal insertion end, the elongated introducer element being formed of a flexible material adapted for insertion into a urethra during a catheterization procedure, the elongated introducer element having at least one slit extending longitudinally along at least a portion of the elongated introducer element;
a sheath having a first end and a second end being inverted relative to the first end of the sheath to define inner and outer sleeve portions and a space therebetween, the inner sleeve portion defining a flow path for urine;

the elongated introducer element being disposed in the space defined between the inner and outer sleeve portions, the inner sleeve portion being extendable through the at least one slit of the elongated introducer element so as to be disposed within the elongated introducer element and cover an inner surface of the elongated introducer element to thereby separate the inner surface of the elongated introducer element from the urine flow path, and the outer sleeve portion extending over an outer surface of the elongated introducer element to thereby separate the outer surface of the elongated introducer element from the urethra.

2. The intermittent catheter assembly of claim 1 further including a holding element associated with the second end of the sheath for extending the inner sleeve portion through the at least one slit of the elongated introducer element.

3. The intermittent catheter assembly of claim 2 wherein the holding element comprises a cord having a first end attached to the second end of the sheath, the cord also having a second end with a finger grip tab attached thereto.

4. The intermittent catheter assembly of claim 2 wherein the sheath and the holding element are formed of a flushable material.

5. The intermittent catheter assembly of claim 2 wherein the sheath and the holding element are formed of a biodegradable material.

6. The intermittent catheter assembly of claim 1 further including an applicator having at least one opening for receiving the elongated introducer element therethrough, and the first end of the sheath being secured to the applicator about the at least one opening.

7. The intermittent catheter assembly of claim 6 wherein the applicator comprises a collar generally surrounding the first end of the sheath and defines a stop during insertion of the elongated introducer element into a urethra.

8. The intermittent catheter assembly of claim 6 wherein the second end of the sheath is secured to generally diametrically opposed portions of the applicator.

9. The intermittent catheter assembly of claim 6 wherein the applicator includes a drainage lumen wherein the second end of the sheath is secured about the drainage lumen so that the urine flow path defined by the inner sleeve portion is in fluid communication with the drainage lumen.

10. The intermittent catheter assembly of claim 9 wherein the drainage lumen is at least partially defined by a drainage tube that extends distally from a distal surface of the applicator.

11. The intermittent catheter of claim 10 wherein the drainage tube functions as a guide for guiding insertion of the elongated introducer element into the at least one opening of the applicator.

12. The intermittent catheter assembly of claim 6 wherein the applicator includes two openings for receiving the elongated introducer element and the elongated introducer element includes a pair of opposed arms wherein each arm is received into one of the openings and into the space defined between the outer and inner sleeve portions.

13. The intermittent catheter assembly of claim 1 wherein the elongated introducer element comprises a tube having a single slit extending along the entire length thereof from the proximal insertion end to the distal end.

14. The intermittent catheter assembly of claim 1 wherein the proximal insertion end of the elongated introducer element is beveled to be at other than a right angle to an axis of the elongated introducer element to aid insertion into a urethra during a catheterization procedure.

15. The intermittent catheter assembly of claim 1 wherein the proximal insertion end of the elongated introducer element is beveled so as to be at an angle of between about 15° and about 30° to an axis of the elongated introducer element.

16. The intermittent catheter assembly of claim 1 wherein the elongated introducer element includes opposed elongated arms defining the slit therebetween.

17. The intermittent catheter assembly of claim 1 wherein the slit extending longitudinally along at least a substantial portion of the length of the elongated introducer element has a width of between about 1.0 mm and 1.5 mm.

18. The intermittent catheter assembly of claim 1 wherein the sheath is formed of a flushable material.

19. The intermittent catheter assembly of claim 1 wherein the sheath is formed of a biodegradable material.

20. An intermittent catheter assembly, comprising:
an elongated introducer element having a proximal insertion end and a distal end remote from the proximal insertion end, the elongated introducer element being formed of a flexible material adapted for insertion into a urethra during a catheterization procedure, the elongated introducer element having at least one slit extending longitudinally along at least a portion of the elongated introducer element;
an applicator having an opening for receiving the elongated introducer element, and a sheath having a first end secured to the applicator about the opening and a second end defining a discharge opening;
the second end of the sheath being inverted relative to the first end of the sheath and extending into the opening in the applicator to define inner and outer sleeve portions wherein the inner sleeve portion defines a flow path for urine through the discharge opening;
a holding element associated with the second end of the sheath for extending the inner sleeve portion through the at least one slit of the elongated introducer element so as to dispose the inner sleeve portion within the elongated introducer element wherein the inner sleeve portion covers an inner surface of the elongated introducer element to thereby separate the inner surface of the elongated introducer element from the urine flow path; and
as the elongated introducer element is inserted through the opening of the applicator, the outer sleeve portion extends over an outer surface of the elongated introducer element.

21. The intermittent catheter assembly of claim 20 wherein the proximal insertion end of the elongated introducer element is beveled to be at other than a right angle to an axis of the elongated introducer element to aid insertion into a urethra during a catheterization procedure.

22. The intermittent catheter assembly of claim 20 wherein the proximal insertion end of the elongated introducer element is beveled so as to be at an angle of between about 15° and about 30° to an axis of the elongated introducer element.

23. The intermittent catheter assembly of claim 20 wherein the elongated introducer element comprises a tube having a single slit extending along the entire length thereof from the proximal insertion end to the distal end.

24. The intermittent catheter assembly of claim 20 wherein the elongated introducer element comprises a pair of opposed elongated arms that define the slit therebetween.

25. The intermittent catheter assembly of claim 20 wherein the slit extending longitudinally along at least a substantial portion of the length of the elongated introducer element has a width of between about 1.0 mm and 1.5 mm.

26. The intermittent catheter assembly of claim 20 wherein the applicator comprises a collar generally surrounding the first end of the thin sheath and also defining a stop during insertion of the elongated introducer element into a urethra.

27. The intermittent catheter assembly of claim 20 wherein the holding element comprises a cord having a first end attached to the second end of the thin sheath, the cord also having a second end with a finger grip tab attached thereto.

28. The intermittent catheter assembly of claim 20 wherein the second end of the thin sheath is secured to generally diametrically opposed portions of the applicator to define the holding element associated with the second end of the sheath.

29. The intermittent catheter assembly of claim 20 wherein the applicator, the sheath and the holding element are formed of a flushable material.

30. The intermittent catheter assembly of claim 20 wherein the applicator, the sheath and the holding element are formed of a biodegradable material.

\* \* \* \* \*